US007939326B2

(12) United States Patent
Olsen et al.

(10) Patent No.: US 7,939,326 B2
(45) Date of Patent: May 10, 2011

(54) METHODS AND COMPOSITIONS FOR ENHANCING CELL ADHESION PROPERTIES

(75) Inventors: John Christian Olsen, Chapel Hill, NC (US); Manij Patel, Durham, NC (US); David Allen Wilcox, Wauwatosa, WI (US)

(73) Assignees: The University of North Carolina at Chapel Hill, Chapel Hill, NC (US); The MCW Research Foundation, Milwaukee, WI (US)

(*) Notice: Subject to any disclaimer, the term of this patent is extended or adjusted under 35 U.S.C. 154(b) by 1205 days.

(21) Appl. No.: 11/118,712

(22) Filed: Apr. 29, 2005

(65) Prior Publication Data

US 2005/0272155 A1    Dec. 8, 2005

Related U.S. Application Data

(60) Provisional application No. 60/566,613, filed on Apr. 29, 2004.

(51) Int. Cl.
*C12N 15/85* (2006.01)
*C12N 5/00* (2006.01)
*C12N 7/00* (2006.01)

(52) U.S. Cl. .............. 435/456; 435/325; 435/235.1

(58) Field of Classification Search .................. 435/455, 435/325, 235.1
See application file for complete search history.

(56) References Cited

U.S. PATENT DOCUMENTS

| | | | | |
|---|---|---|---|---|
| 4,650,764 A | * | 3/1987 | Temin et al. ............ | 435/240 |
| 5,091,309 A | * | 2/1992 | Schlesinger et al. ........ | 435/69.1 |
| 5,240,846 A | * | 8/1993 | Collins et al. ............ | 435/240 |
| 5,501,979 A | * | 3/1996 | Geller et al. ............ | 435/320 |
| 5,576,206 A | * | 11/1996 | Schlegel .................... | 435/240.2 |
| 5,817,491 A | * | 10/1998 | Yee et al. .................. | 435/172.3 |
| 6,013,516 A | * | 1/2000 | Verma et al. ............ | 435/325 |
| 6,214,834 B1 | | 4/2001 | Jadhav et al. | |

FOREIGN PATENT DOCUMENTS

| | | | |
|---|---|---|---|
| CN | 2483951 Y | | 4/2002 |
| EP | 0 453 242 A1 | * | 4/1991 |
| EP | 0 611 822 | * | 8/1994 |
| WO | WO 91/19798 | * | 12/1991 |
| WO | WO/95/14091 | * | 5/1995 |
| WO | WO/95/27044 | * | 10/1995 |
| WO | WO/95/31565 | * | 11/1995 |
| WO | WO/96/27672 | * | 9/1996 |
| WO | WO/96/35454 | * | 11/1996 |
| WO | WO/96/35777 | * | 11/1996 |
| WO | WO/96/35798 | * | 11/1996 |
| WO | WO/96/36364 | * | 11/1996 |
| WO | WO/97/12622 | * | 4/1997 |
| WO | WO/98/17815 | * | 4/1998 |
| WO | WO/98/17816 | * | 4/1998 |
| WO | WO 99/51639 | | 10/1999 |
| WO | WO 01/79518 A3 | | 10/2001 |
| WO | WO 2004/067724 | | 8/2004 |

OTHER PUBLICATIONS

Olsen et al, (Gene Therapy, 5: 1481-1487, 1998.*
Johnson et al, Methods in Molecular Biology, vol. 229, Lentivirus Gene Engineering Protocols, edited by: M. Frederico, Humana Press Inc. Totowa, NJ, p. 181-196, 2003).*
Logan et al, Current Opinion in Biotechnology, 13: 429-436, 2002.*
Brassard et al (Experimental Cell Research, 251: 33-45, 1999).*
Klages et al (Molecular Therapy (2(2): 170-176, 2000).*
Chuntharapai et al., "Blocking Monoclonal Antibodies to αVβ3 Integrin: A Unique Epitope of αVβ3 Integrin Is Present on Human Osteoclasts", *Experimental Cell Research* 205, 345-352 (1993).
Nishimura et al., "Interaction with Vitronectin and Functional Divergence of the β8 Cytoplasmic Domain", *The Journal of Biological Chemistry*, vol. 269, No. 46, Issue of Nov. 18, pp. 28708-28715, 1994.
JC Olsen, "Gene Transfer Vectors Derived from Equine Infectious Anemia Virus", *Gene Therapy*, (1998) 5, pp. 1481-1487.
Saito and Sugano, "Methods of Cogenesis and Experimental Methods for Manifestation Analysis" from the Protocol Series, Supplement to Experimental Medicine, Publishers: Kassai Bunmei, Yodosha, Ltd., Sep. 1, 1992.
Cohen; New Role for HIV: A Vehicle for Moving Genes Into Cells; *Science*, vol. 272:195 (1996).
Friedmann; Progress Toward Human Gene Therapy; *Science*, vol. 244:1275-81 (1989).
Hart, et al.; Reduced Retroviral Entry Into Polarized Airway Epithelia; *1996 Cystic Fibrosis Conference*, Abstract No. 246.
Johnson, et al.; In Vivo Airway Gene Transfer and in Vitro Correction of CF Airway Cells Without Selection by a VSV-G Pseudotyped Retroviral Vector, *1996 Cystic Fibrosis Conference*, Abstract No. 247.
Landau, et al.; Packaging System for Rapid Production of Murine Leukemia Virus Vectors with Variable Tropism; *Virology*, vol. 66, No. 8:5110-13 (1992).
Naldini, et al.; In Vivo Gene Delivery and Stable Transduction of Nondividing Cells by a Lentiviral Vector; *Science*, vol. 272:263-67 (1996).
Pear, et al.; Production of high-titer helper-free retroviruses by transient transfection; *Proc. Natl. Acad. Science*, vol. 90:8392-96 (1993).
Perry, et al.; The Surface Envelope Protein Gene Region of Equine Infectious Anemia Virus Is Not an Important Determinant of Tropism In Vitro; *Virology*, vol. 66, No. 7:4085-97 (1992).
Tan, et al.; Inhibitory Activity of the Equine Infectious Anemia Virus Major 5' Splice Site in the Absence of Rev; *Virology*, vol. 70, No. 6:3645-58 (1996).
Ory et al.; A stable human-derived packaging cell line for production of high titer retrovirus/vesicular stomatitis virus G pseudotypes, *Proc. Natl Acad Sci USA*, 93:11400-11406 (1996).

(Continued)

*Primary Examiner* — Thaian N Ton
*Assistant Examiner* — Magdalene Sgagias
(74) *Attorney, Agent, or Firm* — Myers Bigel Sibley & Sajovec, P.A.

(57) ABSTRACT

The present invention provides a modified cell having adhesion properties that are increased as compared to the adhesion properties of an unmodified cell, comprising a) a recombinant nucleic acid encoding an integrin $\beta_3$ subunit; b) a recombinant nucleic acid encoding an integrin $\alpha_v$ subunit; c) a recombinant nucleic acid encoding an integrin $\alpha_{IIb}$ subunit; and/or d) any combination of (a), (b) and (c).

15 Claims, 11 Drawing Sheets

OTHER PUBLICATIONS

Weiss; Retrovirus classification and cell interactions, *Journal of Antimicrobial Chemotherapy*, 37:1-11 (1996).

Maury et al.; Cellular and Viral Specificity of Equine Infectious Anemia Virus Tat Transactivation, *Virology*, 200:632-642 (1994).

Zufferey et al.; Multiply attenuated lentiviral vector achieves efficient gene delivery in vivo, *Nature Biotechnology*, 15:871-875 (1997).

International Search Report PCT/US/98/10144 mailed Sep. 25, 1998.

International Search Report, PCT/GB 97/02857 mailed Mar. 17, 1998.

Richardson, Helper virus-free transfer of human immunodeficiency virus type I vectors, *Journal of General Virology*, 76, 691-696 (1995).

Hynes, Integrins: Bidirectional, Allosteric Signaling Machines, *Cell*, 110: 673-687 (2002).

Ling et al., Role of Integrin $\alpha v\beta 3$ in the Production of Recombinant Adenoviruses in HEK-293 Cells, *Gene Therapy*, 9: 907-914 (2002).

Vancha et al., Use of Polyethyleneimine Polymer in Cell Culture as Attachment Factor and Lipofection Enhancer, *BMC Biotechnology*, 4, 23 (2004).

Ryu et al., Suspension Culture of Anchorage-Dependent Animal Cells Using Nanospheres of the Biodegradable Polymer, Poly (lactic-co-glycolic acid), *Biotechnology Letters*, 25: 1363-1367 (2003).

Ryu et al., HEK 293 Cell Suspension Culture Using Fibronectin-Adsorbed Polymer Nanospheres in Serum-Free Medium, *J Biomed Mater Res*, 71A: 128-133 (2004).

Conesa et al., Down-Regulation of $\alpha v/\beta 3$ Integrin via Misrouting to Lysosomes by Overexpression of a $\beta 3$Lamp 1Fusion Protein, *Biochemical Journal*, 370: 703-711 (2003).

Krivacic et al. 2003. "Extracellular Matrix Conditions T Cells for Adhesion to Tissue Interstitium" *The Journal of Immunology* 170:5034-5044.

Yamada et al. 2003. "Dimensions and Dynamics in Integrin Function" *Brazilian Journal of Medical and Biological Research* 36:959-966.

Villavicencio-Lorini et al. 2002. "Biochemical Engineering of the Acyl Side Chain of Sialic Acids Stimulates Integrin-Dependent Adhesion of HL60 Cells to Fibronection" *J Mol Med* 80:671-677.

Lee et al. 2004. "Importance of Integrin $\beta 1$-Mediated Cell Adhesion on Biodegradable Polymers Under Serum Depletion in Mesenchymal Stem Cells and Chondrocytes" *Biomaterials* 25:1901-1909.

Wilcox et al. 1999. "Integrin $\alpha$IIb Promoter-Targeted Expression of Gene Products in Megakaryocytes Derived From Retrovirus-Transduced Human Hematopoietic Cells" *PNAS USA* 96:9654-9659.

International Search Report for PCT Application No. PCT/US2005/015120, mailed Dec. 12, 2005.

* cited by examiner

METHODS AND COMPOSITIONS FOR ENHANCING CELL ADHESION PROPERTIES

PRIORITY CLAIM

This application claims the benefit, under 35 U.S.C. §119 (e), of U.S. Provisional Application No. 60/566,613, filed Apr. 29, 2004, the entire contents of which are incorporated by reference herein.

STATEMENT OF GOVERNMENT SUPPORT

Research related to this invention was supported, at least in part, by U.S. Government Grant No. HL 51818 awarded by NIH/NHLBI. The Government has certain rights in this invention.

BACKGROUND OF THE INVENTION

1. Field of the Invention

The present invention relates to modified cells with enhanced adherence properties in a cell culture environment and methods of making and using these cells.

2. Background Art

Human embryonic kidney (HEK) 293 cells is one example of a variety of different cells that are widely used both commercially and in research largely due to their ease of growth and their ability to be efficiently transfected with foreign DNA. However, one problem with derivatives of 293 cells and various other cells is that they often adhere poorly to tissue culture vessels. This makes manipulation of these cells difficult. One way to overcome this problem is to coat cell culture vessels with vitronectin or polylysine, which effects both the cost and ease of handling of such cell cultures, making this approach undesirable for large scale production of cells.

The present invention overcomes previous shortcomings in the art by providing methods and compositions whereby cells can be modified to express integrins on the cell surface to enhance adherence to tissue culture substrates.

SUMMARY OF THE INVENTION

Figure 1:
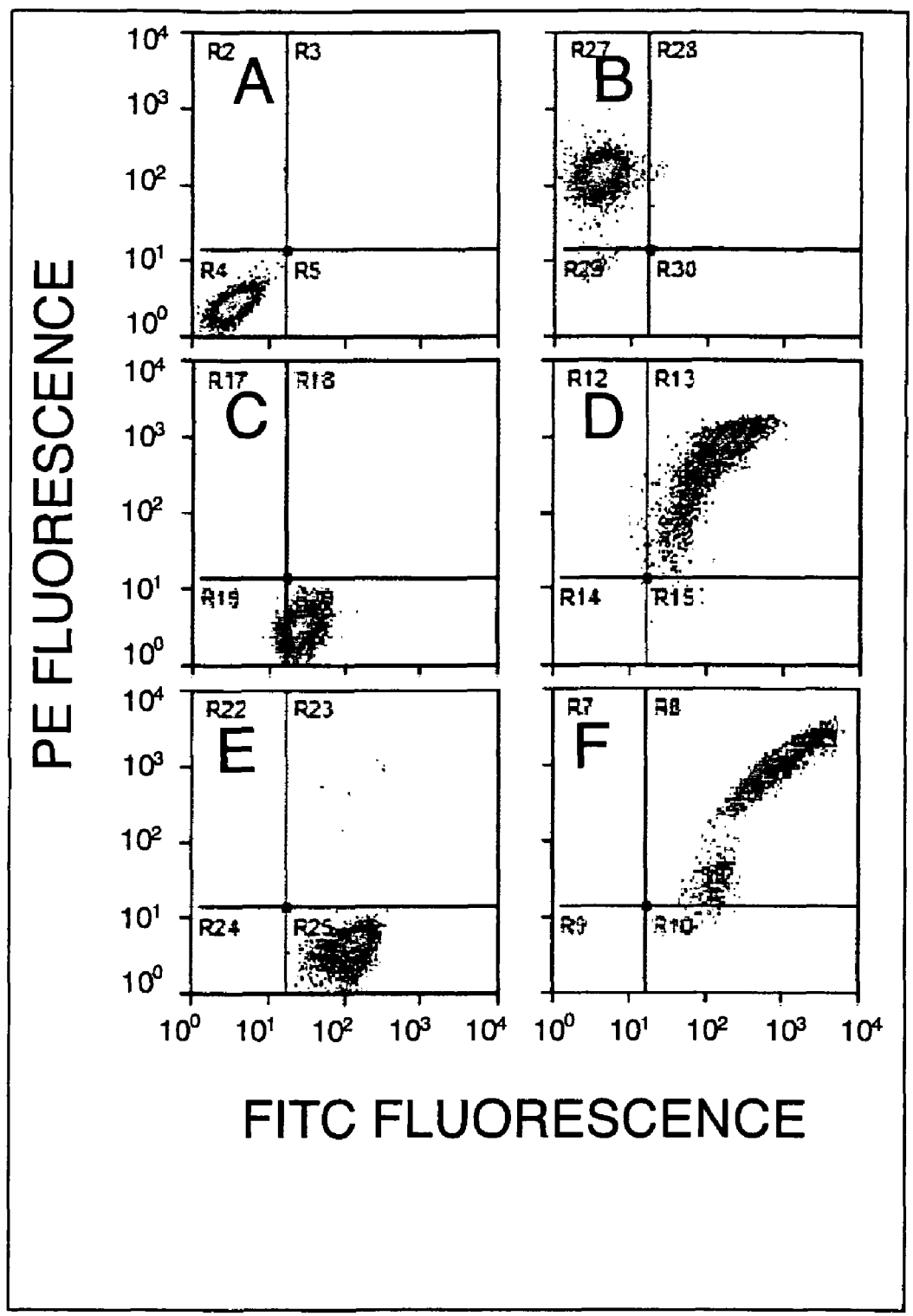
FIGS. 1A-F. Cell surface expression of human integrin cDNAs in B-241 cells. B-241 cell lines, stably transfected with various human integrin cDNAs were trypsinized from tissue culture plates. Intact living cells were stained with mouse monoclonal antibodies conjugated to either fluorescein (FITC) for detection of α subunits or phycoerytherin (PE) for detection of $\beta_3$ subunit. Antibodies used were specific for human $\beta_3$ integrin (BD Biosciences, catalog number 555754), human $\alpha_v$ integrin (Chemicon International, Inc., catalog number CBL490F) and human platelet glycoprotein (GP) IIb also known as integrin $\alpha_{IIb}$ integrin subunit (Chemicon International, Inc., catalog number CBL589F). The panels show fluorescence profiles of the various B-241 cell line derivatives. Panel A: unmodified B-241 cells. Panel B: cells modified to express human platelet GPIIIa also known as $\beta_3$ integrin subunit. Panel C: cells modified to express human IIb integrin subunit. Panel D: cells modified to express $\alpha_{IIb}\beta_3$ integrin receptor for several extracellular matrix molecules including: fibrinogen, von Willebrand factor, fibronectin and vitronectin. Panel E: cells modified to express $\alpha_v$ integrin subunit. Panel F: cells modified to express $\alpha_v\beta_3$ receptor for vitronectin.

In one embodiment, the present invention provides a modified cell having adhesion properties increased at least three fold as compared to the adhesion properties of an unmodified cell, comprising, consisting of or consisting essentially of, a recombinant nucleic acid that can be a) a nucleic acid encoding an integrin $\beta_3$ subunit; b) a nucleic acid encoding an integrin $\alpha_v$ subunit; c) a nucleic acid encoding an integrin $\alpha_{IIb}$ subunit; and/or d) any combination of (a), (b) and (c).

Further provided herein is a 293.01 cell, comprising, consisting of, and/or consisting essentially of, a recombinant nucleic acid that can be a) a nucleic acid encoding an integrin $\beta_3$ subunit; b) a nucleic acid encoding an integrin $\alpha_v$ subunit; c) a nucleic acid encoding an integrin $\alpha_{IIb}$ subunit; and/or d) any combination of (a) and (b) and (c).

The present invention additionally provides a method of adhering a cell to a surface of a culture vessel, comprising, consisting of, or consisting essentially of: a) introducing into the cell a nucleic acid that can be i) a nucleic acid encoding an integrin $\beta_3$ subunit; ii) a nucleic acid encoding an integrin $\alpha_v$ subunit; iii) a nucleic acid encoding an integrin $\alpha_{IIb}$ subunit; and/or iv) any combination of (i), (ii) and (iii); and b) contacting the cell of (a) with the surface of the culture vessel under conditions whereby the cell can adhere to the surface of the culture vessel.

In yet further embodiments, the present invention provides a method of producing a modified cell having adhesion properties increased at least three fold as compared to the adhesion properties of an unmodified cell, comprising, consisting of, or consisting essentially of: introducing into the cell a recombinant nucleic acid that can be a) a nucleic acid encoding an integrin $\beta_3$ subunit; b) a nucleic acid encoding an integrin $\alpha_v$ subunit; c) a nucleic acid encoding an integrin $\alpha_{IIb}$ subunit; and/or d) any combination of (a), (b) and (c).

Also provided herein is a method of producing virus particles in cells in a culture vessel, comprising, consisting of, or consisting essentially of: a) introducing into the cells a recombinant nucleic acid selected from the group consisting of: i) a nucleic acid encoding an integrin $\beta_3$ subunit; ii) a nucleic acid encoding an integrin $\alpha_v$ subunit; iii) a nucleic acid encoding an integrin $\alpha_{IIb}$ subunit; and iv) any combination of (i) and (ii) and (iii); b) placing the cells of (a) into the culture vessel; and c) introducing infectious virus particles into the culture vessel of (b) under conditions whereby virus particles are produced.

Furthermore, a method of producing recombinant lentivirus particles in 293.101 cells in a culture vessel is provided, comprising, consisting of, or consisting essentially of: a) introducing into the 293.101 cells a recombinant nucleic acid that can be i) a nucleic acid encoding an integrin $\beta_3$ subunit; ii) a nucleic acid encoding an integrin $\alpha_v$ subunit; iii) a nucleic acid encoding an integrin $\alpha_{IIb}$ subunit; and/or iv) any combination of (i) and (ii) and (iii); b) placing the cells of (a) into the culture vessel; and c) introducing into the cells of (b): I) a first vector comprising, consisting of, or consisting essentially of, a lentivirus nucleic acid sequence encoding lentivirus gag and lentivirus pol, wherein said vector (1) comprises at least one defect in at least one gene encoding a lentivirus structural protein, and (2) comprises a defective packaging signal; II) a second vector comprising, consisting of, or consisting essentially of, a lentivirus nucleic acid sequence comprising cis-acting sequence elements required for reverse transcription of the vector genome wherein said vector (1) comprises a competent packaging signal, (2) comprises a heterologous gene; and III) a third vector comprising, consisting of, or consisting essentially of, a nucleic acid sequence of a virus, wherein said third vector (1) expresses a viral envelope protein, and (2) comprises a defective packaging signal, under conditions whereby recombinant lentivirus particles are produced.

Additionally provided herein is a method of making a packaging cell, comprising, consisting of, or consisting essentially of, transfecting a modified cell of this invention with a vector comprising, consisting of, or consisting essentially of, a lentivirus nucleic acid sequence, wherein the vector comprises a defective packaging signal.

In an additional embodiment, the present invention provides a packaging cell comprising a modified cell of this invention, wherein the cell comprises a lentivirus nucleic acid sequence encoding at least one lentivirus structural protein, wherein the nucleic acid sequence is packaging-signal defective, such that the cell itself produces at least one lentivirus structural protein, but does not produce replication-competent infectious virus.

Various other objectives and advantages of the present invention will become apparent from the following detailed description.

DETAILED DESCRIPTION OF THE INVENTION

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The present invention is based on the unexpected discovery that modifying cells to express integrins resulted in cells that adhered much more strongly to tissue culture substrates than unmodified cells.

Thus, in one embodiment, the present invention provides a modified cell having adhesion properties increased as compared to the adhesion properties of an unmodified cell, comprising a recombinant nucleic acid that can be a) a nucleic acid encoding an integrin $\beta_3$ subunit; b) a nucleic acid encoding an integrin $\alpha_v$ subunit; c) a nucleic acid encoding an integrin $\alpha_{IIb}$ subunit; and/or d) any combination of (a), (b) and (c). The cell is maintained under conditions whereby the integrin subunit coding sequences are expressed and/or over-expressed in the cell. In some embodiments, the integrin subunit coding sequences are transiently expressed in the cell according to methods well known in the art to regulate nucleic acid expression, such that the timing and/or amount of expression of nucleic acid encoding an integrin subunit of this invention can be controlled.

The amount of increase in adhesion properties can be at least two-fold, at least three-fold, at least four-fold, at least five-fold, at least six-fold, at least seven-fold, at least eight-fold, at least nine-fold, or at least ten-fold, as compared to the adhesion properties of an unmodified cell. The increase in adhesion properties is measured by contacting cells, either modified as described herein, or unmodified, with a tissue culture substrate [e.g., plastic (e.g., polypropylene, polyethylene, polyacrylate, polysorbate, etc.), glass, agar, collagen, fibronectin, ceramic, metal, biodegradable or nonbiodegradable polyester scaffolds, tubing, etc.] for a period of time sufficient to allow the cells to adhere to the substrate, and determining the amount of cells that are adhered to the substrate, according to the methods described herein, as well as any art-known method for quantifying cells. Modified cells that adhere to the tissue culture substrate in greater numbers than unmodified cells are cells that have increased adhesion properties. The increase in adhesion properties correlates with the increased number of adhered cells and can be expressed as an X-fold increase (e.g., two-fold; three-fold, etc.) as a percentage (e.g., 10% increase in adherence properties based on 10% more modified cells adhered to substrate as compared to unmodified cells), and/or according to any other art-known value that identifies an increase relative to a baseline measurement.

The cells of this invention can be any type of cell that can be grown and/or maintained under culture conditions and can take up and express recombinant nucleic acid encoding an integrin. For example, a cell of this invention can be, but is not limited to, a BiG-45 cell, a 293.101 cell, a B-241 cell, a 293T cell, a HEK 293 cell, a Dami cell, a Chinese hamster ovary cell, a hybridoma cell, HUVEC, and MS-5 cells.

A cell of this invention can be present singly or in a population of cells and a cell of this invention can be contained in a tissue culture vessel, which can be, but is not limited to, a flask, a bottle, a roller bottle, a vial, a tube, a chamber, a flask, a dish, a slide, a plate, a tissue culture well, which can be present as a single well or in multiple well plates and/or any combination thereof.

A cell of this invention is modified by the introduction of a recombinant nucleic acid encoding an integrin, which can be a human integrin, and can be but is not limited to an integrin $\beta_3$ subunit, an integrin $\alpha_v$ subunit, an integrin $\alpha_{IIb}$ subunit, and/or any combination of these integrin subunits, in any order. The present invention further provides any combination of integrins that bind to extracellular matrix molecules that can be coated or secreted by cells onto substrates upon which cells grow. Some examples include, but are not limited to, collagen receptor $\alpha 2$-$\beta 1$, laminin receptor a 6-$\beta 4$, several of vitro nectin receptors $\alpha V$-$\beta 5$, and $\beta 1$, which can be combined with various $\alpha$ subunits for receptor extracellular matrix molecules such as fibronectin. The integrins of this invention can be from any species, such as chicken, dog, mouse, and rat, as some examples. The nucleic acid encoding these integrins can be introduced into a cell on one or more than one nucleic acid constructs from which the nucleic acid is expressed to produce the integrin protein within the cell.

"Nucleic acid" as used herein refers to single- or double-stranded molecules that may be DNA, comprised of the nucleotide bases A, T, C and G, or RNA, comprised of the bases A, U (substitutes for T), C, and G. The nucleic acids of this invention can represent a coding strand or its complement. Nucleic acids of this invention can comprise a nucleotide sequence that can be identical in sequence to the sequence which is naturally occurring or, due to the well-characterized degeneracy of the nucleic acid code, can include alternative codons which encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide is retained. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and/or function (i.e., biological activity) of the polypeptide encoded by the nucleic acid are maintained.

A "recombinant" nucleic acid is one that has been created using genetic engineering techniques, which are well known in the art.

By the term "express" or "expression" (and grammatical equivalents thereof) of a nucleic acid sequence, it is meant that the sequence is transcribed, and optionally, translated.

The nucleic acid encoding an integrin of this invention can further comprise a promoter that directs expression of the integrin within the cell. Thus, in certain embodiments, the promoter can be operably linked to the recombinant nucleic acid encoding the integrin(s). The promoter can be a constitutive promoter, resulting in constitutive expression of the integrin nucleic acid in the cell, or the promoter can be an inducible promoter, resulting in expression of the integrin nucleic acid in the cell only in the presence of an inducible element that activates the promoter, thereby allowing the production of integrin proteins from the recombinant nucleic acid to be controlled.

Examples of a promoter of this invention include, but are not limited to, CMV immediate early promoter, Rous sarcoma virus promoter, elongation factor 1α, βactin, eukaryotic initiation factor 4A1, composite CMV enhancer/βactin promoter (CAG), composite elongation factor 1α promoter/HTLV 5' untranslated region, composite SV40 enhancer/human ferritin heavy chain-elongation factor 1α promoter, composite CMV enhancer/human ferritin light chain elongation factor 1α promoter and composite CMV promoter/tetracycline operator. The promoters of this invention can be present on the recombinant nucleic acid(s) of this invention in any combination and/or order.

A nucleic acid of this invention can be introduced into a cell according to methods well known in the art, including, but not limited to transduction (e.g., infection by a viral vector), transfection (electroporation, lipofection, calcium phosphate precipitation, microinjection, etc.).

In certain embodiments, the present invention provides a 293.01 cell comprising a recombinant nucleic acid that can be a) a nucleic acid encoding an integrin $\beta_3$ subunit; b) a nucleic acid encoding an integrin $\alpha_v$ subunit; c) a nucleic acid encoding an integrin $\alpha_{IIb}$ subunit; and/or d) any combination of (a) and (b) and (c). As noted herein, the nucleic acids encoding the integrins can be present on the same or different constructs in any order and/or combination and can be introduced into the cell simultaneously and/or sequentially. The nucleic acids can also be expressed simultaneously and/or in any order and/or combination.

In a particular embodiment, the present invention provides a 293.101 cell comprising a recombinant nucleic acid encoding an integrin $\beta_3$ subunit and a recombinant nucleic acid encoding an integrin $\alpha_v$ subunit. These recombinant nucleic acids can be present on the same or different constructs and can be introduced into the cell simultaneously and/or sequentially in any combination and/or order and can be expressed simultaneously and/or in any order.

Further provided herein are various methods for producing the cells of this invention. Thus, in one embodiment, the present invention provides a method of adhering a cell to a surface of a culture vessel, comprising: a) introducing into the cell a nucleic acid that can be i) a nucleic acid encoding an integrin $\beta_3$ subunit; ii) a nucleic acid encoding an integrin $\alpha_v$ subunit; iii) a nucleic acid encoding an integrin $\alpha_{IIb}$ subunit; and/or iv) any combination of (i), (ii) and (iii); and b) contacting the cell of (a) with the surface of the culture vessel under conditions whereby the cell can adhere to the surface of the culture vessel.

The conditions whereby a cell can adhere to the surface of a culture vessel are described herein and are well known in the art for any given cell type, based on the medium included in the culture vessel, as well as the environment in which the culture vessel is maintained (e.g., temperature, humidity, carbon dioxide content, etc.). Medium formulations and culture conditions for the cell types of this invention are well established in the art. As one example, HEK 293 cells are grown and maintained in culture under the following conditions: HEK 293 cells are cultured in Dulbecco's Modified Eagle's Medium (DMEM catalog number 11995-065, Invitrogen Corp) containing 10% fetal bovine serum at 37° C. and in a 5% $CO_2$ incubator. When cells become 90% confluent, they are passaged for maintenance at a 1:6 dilution.

Additionally provided herein is a method of producing a modified cell having adhesion properties increased at least two-fold, at least three-fold and/or at least four-fold as compared to the adhesion properties of an unmodified cell, comprising: introducing into the cell a recombinant nucleic acid that can be a) a nucleic acid encoding an integrin $\beta_3$ subunit; b) a nucleic acid encoding an integrin $\alpha_v$ subunit; c) a nucleic acid encoding an integrin $\alpha_{IIb}$ subunit; and d) any combination of (a), (b) and (c).

The cells of the present invention are shown herein to better withstand treatments (such as glycerol shock or DMSO shock) that are commonly used in transient transfection protocols to increase nucleic acid uptake. Thus, in further embodiments, the present invention provides a cell of this invention having an enhanced ability to take up nucleic acid and further provides methods of making such cells according to the protocols described herein, as well as methods of using such cells for the production of virus particles, with modifications as described herein to accommodate the enhanced ability to withstand treatments used in transfection protocols.

The cells of this invention can be used for a variety of commercial and research applications, including the production of various materials (e.g., proteins, viruses, etc.) within the cells, the yield of which is improved because of the increased number of cells in a culture vessel available for production due to increased adherence properties. Thus, in certain embodiments, the present invention provides a method of producing virus particles in cells in a culture vessel, comprising; a) introducing into the cells a recombinant nucleic acid that can be i) a nucleic acid encoding an integrin $\beta_3$ subunit; ii) a nucleic acid encoding an integrin $\alpha_v$ subunit; iii) a nucleic acid encoding an integrin $\alpha_{IIb}$ subunit; and/or iv) any combination of (i) and (ii) and (iii); b) placing the cells of (a) into the culture vessel; and c) introducing infectious virus particles into the culture vessel of (b) under conditions whereby virus particles are produced.

The virus of this invention can be any virus that can be produced in cell culture, including, but not limited to, lentivirus, retrovirus, paramyxovirus, orthomyxovirus, flavivirus, adenovirus, adeno-associated virus (AAV), rhabdovirus, picornavirus, alphavirus, coronavirus, herpesvirus, papovavirus, bunyavirus, orbivirus, poxvirus, arenavirus, herpesvirus, hepadnavirus and filovirus, as well as any other virus now known or later identified that can be produced in cell culture.

In certain embodiments of this invention, the virus can be a lentivirus, which can be a primate lentivirus (e.g., HIV-1, HIV-2, SIV), a non-primate lentivirus (e.g., FIV, BLV, EIAV, CEV and visna virus), and/or any other lentivirus now known or later identified.

Thus, the present invention further provides a method of producing recombinant lentivirus particles in cells in a culture vessel, comprising: a) introducing into the cells a recombinant nucleic acid that can be i) a nucleic acid encoding an integrin $\beta_3$ subunit; ii) a nucleic acid encoding an integrin $\alpha_v$ subunit; iii) a nucleic acid encoding an integrin $\alpha_{IIb}$ subunit; and/or iv) any combination of (i) and (ii) and (iii); b) placing the cells of (a) into the culture vessel; and c) introducing into the cells of (b): I) a first vector comprising a lentivirus nucleic acid sequence encoding one or more lentivirus structural proteins, wherein said vector (1) comprises at least one defect in at least one gene encoding a lentivirus structural protein, and (2) comprises a defective packaging signal; II) a second vector comprising a lentivirus nucleic acid sequence comprising cis-acting sequence elements required for reverse transcription of the vector genome wherein said vector comprises a competent packaging signal, and III) a third vector comprising a nucleic acid sequence of a virus, wherein said third vector (1) expresses a viral envelope protein, and (2) comprises a defective packaging signal, under conditions whereby recombinant lentivirus particles are produced.

In certain embodiments, the second vector of the above method can be deficient for expression of at least one lentivirus structural protein (e.g., gag, pol or env). In other embodiments, the first vector can be a gag-pol expression vector, which has no env gene or has an env gene that comprises a defect that renders it incapable of being expressed from the first vector. The defect in the env gene can be a deletion, substitution and/or addition mutation that renders the gene unable to be expressed from the first vector.

In other embodiments, the first and second vector can both lack an env gene or both can comprise an env gene comprising a defect that can be a deletion, substitution and/or addition mutation that renders the gene unable to be expressed from the first vector.

The third vector of the method described above can comprise nucleic acid encoding a viral envelope protein, which nucleic acid can be a lentivirus env gene and/or the third vector can comprise nucleic acid that encodes a virus envelope protein that is not a lentivirus envelope protein. For example, the envelope protein encoded by the nucleic acid of the third vector can be the vesicular stomatitis virus G (VSV-G) glycoprotein.

The second vector of the method described above can comprise a multiple cloning site into which a heterologous nucleic acid sequence can be inserted and/or one or more heterologous nucleic acids. A heterologous nucleic acid of this invention can encode a protein or peptide, which can be antigenic, immunogenic and/or therapeutic when produced in a cell into which the heterologous nucleic acid is introduced.

The term "heterologous nucleic acid" is a well known term of art and would be readily understood by one of skill in the art to be a nucleic acid that is not normally present within the cell into which it has been introduced and/or is a nucleic acid that is expressed under the control of regulatory elements that are not normally present within the cell. A heterologous nucleic acid of this invention can also be a nucleic acid that is present in an amount, or expressed in an amount, that is not normally the amount present in the cell into which the nucleic acid has been introduced. A "heterologous nucleic acid" will typically be a sequence that is not naturally occurring in the cell. Alternatively, a heterologous nucleotide sequence can refer to a sequence that is placed into a non-naturally occurring environment (e.g., by association with a promoter with which it is not naturally associated).

The first vector, the second vector, and the third vector of this invention can be produced according to standard methods of manipulating nucleic acid sequences to produce vector constructs and, in certain embodiments, the first, second and/or third vector of this invention can be obtained from cDNA clones of the lentivirus genome.

As some examples, the first vector of this invention can be the plasmid pEV53, the plasmid pEV53A and/or the plasmid pEV53B; the second vector of this invention can be the plasmid pEC-lacZ, the plasmid pEC-puro, the plasmid pESIN6.1CpuroW, the plasmid pESIN6.1G3W, the plasmid pE11.1G3W and/or the plasmid pESIN11.1G3W; and the third vector of this invention can be the plasmid pCI-VSV-G.

pEV53B is similar to pEV53 except that all EIAV leader sequences up to 3 nt upstream of the major splice donor site have been removed. To construct pEV53B, the gag gene and part of pol was amplified from pEV53 by PCR using the primers: 5'-TTT<u>GGCGCGCC</u>AGGTAAGATGGGAGAC-CCTTTGAC-3' (forward) (SEQ ID NO:1) and 5'-CTACT-TGATCCTTCTCCTTGAC-3' (reverse) (SEQ ID NO:2). An AscI restriction site (underlined) was included in the forward primer for cloning purposes. The ATG translation start site for gag in the forward primer is indicated in bold and EIAV sequences are shown in italic for the forward primer. The resulting 1.4 kb PCR product was digested with AscI and BsrGI and cloned into AscI-BsrGI digested pEV53A. This resulted in pEV53B. Sequence analysis was used to verify that the gag-pol sequences amplified by PCR were correct.

An example of a second vector of this invention is the plasmid pESIN6.1CpuroW, a 6866 bp plasmid derived from EIAV that expresses the *Streptomyces alboniger* puromycin reporter gene. The plasmid contains two CMV immediate-early enhancer/promoter regions (located at bp 1-734 and 1863-2384); R-U5 sequence domains from the EIAV long terminal repeat (LTR) (bp 735-857); a leader sequence containing the EIAV RNA encapsidation signal (~bp 870-1200), a mutated tat translation start site (CTG to TAG at bp 909-911), a splice donor site at bp 996-997, a mutated gag translation start site (ATG to TAG at bp 1000-1003, a partial EIAV gag sequence (bp 1004-1200); a 'DNA flap' sequence containing the EIAV central polypurine tract (bp 1314-1330) and central termination signal sequence (bp 1422-1448); a puromycin coding sequence (bp 2480-3105); a woodchuck hepatitis virus post-transcriptional regulatory element (bp 3110-3996); an EIAV Self-INactivating (SIN) LTR sequence deleted of EIAV enhancer/promoter sequences (bp 4037-4183); a phage f1 region (bp 4280-4735); an ampicillin resistance coding region (bp 5174-6034); and a ColE1 origin of DNA replication (bp 5554-6228).

Another example of a second vector is pE6.1CpuroW, which is similar to pESIN6.1CpuroW except that the SIN LTR is replaced with the wild-type EIAV LTR. Other examples include pESIN6.1CW and pE6.1CW, which are similar to pESIN6.1CpuroW and pESIN6.1CpuroW, respectively, except that the puromycin resistance gene has been replaced by an expanded multiple cloning site for convenient insertion of other genes or sequences of interest. Further improvements of second vectors are possible; for example, pESIN11.1CW and pE11.1CW are examples of vectors whose leader region has been re-arranged and optimized to provide higher titers.

The lentivirus particles produced according to the methods of this invention are capable of infecting a cell and carrying out a single round of replication in the process of delivering a heterologous nucleic acid to a target cell. An aspect of this technology is a nucleic acid delivery system that excludes the transfer of viral genes to the target cell. This is accomplished by physically separating vectors encoding viral structural proteins from the vector encoding the heterologous nucleic acid. The separate vectors are introduced into a permissive cell (a "packaging cell"). The viral structural proteins are necessary for the production of virus particles, but the genes encoding these proteins are present on vectors that contain a defective packaging signal or no packaging signal, so that the structural protein genes are not packaged into the virus particles produced in the packaging cells. The resulting lentivirus particles are "replication defective" in that the packaged vector does not contain nucleic acid encoding all of the virus structural proteins required for particle assembly.

Thus, in further embodiments, the present invention provides a method of making a packaging cell, comprising transfecting a modified cell of this invention with a vector comprising a lentivirus nucleic acid sequence, wherein the vector comprises a defective packaging signal. The vector can be a gag-pol expression vector and in certain embodiments, the vector can be the plasmid pEV53B.

Additionally provided herein is a packaging cell comprising a modified cell of this invention, wherein the cell comprises a lentivirus nucleic acid sequence encoding at least one lentivirus structural protein, wherein the nucleic acid sequence is packaging-signal defective, such that the cell itself produces at least one lentivirus structural protein, but does not produce replication-competent infectious virus.

In particular, with regard to lentivirus vectors of this invention, in certain embodiments, the vectors are derived from EIAV. Native EIAV nucleic acid can be isolated from cells infected with the virus, and vectors prepared therefrom. An exemplary method for preparing EIAV vectors is provided in Perry et al., *J. Virol.* 66:4085-4097 (1992). For example, cDNA can be produced from EIAV RNA by reverse transcriptase, using methods known in the art. Double-stranded EIAV cDNA can then be produced and cloned into a cloning vector, such as a bacterial cloning vector. Any cloning vector, such as bacterial, yeast or eukaryotic vectors, known and used by those skilled in the art, can be used. In some embodiments, the vectors of the present invention can comprise cDNA molecules that can comprise one or more nucleic acid sequences that are complementary to at least part of a EIAV genome and comprising part of the RNA genome required for replication of the genome, with the cDNA molecule being placed under transcriptional control of a promoter that is functional in the target cell.

A promoter of the present invention can comprise a promoter of eukaryotic and/or prokaryotic origin, sufficient to direct the transcription of a distally located sequence (i.e., a sequence linked to the 5' end of the promoter sequence) in a cell. The promoter region can also include control elements for the enhancement or repression of transcription. Examples of suitable promoters are the cytomegalovirus immediate early promoter (pCMV), the Rous Sarcoma vin's long terminal repeat promoter (pRSV), and the SP6, T3, or T7 promoters. Enhancer sequences upstream from the promoter or terminator sequences downstream of the coding region can optionally be included in the vectors of the present invention to facilitate expression. Vectors of the present invention can also contain additional nucleic acid sequences, such as a polyadenylation sequence, a localization sequence and/or a signal sequence, sufficient to permit a cell to efficiently and effectively express the heterologous nucleic acid of the vector. Examples of possible polyadenylation sequences are the SV40 early region polyadenylation site (Hall et al., *J. Molec. App. Genet.* 2:101 (1983)) and the SV40 late region polyadenylation site (Carswell and Alwine, *Mol. Cell Biol.* 9:4248 (1989)). Such additional sequences are inserted into the vector such that they are operably linked with the promoter sequence, if transcription is desired, or additionally with the initiation and processing sequence if translation and processing are desired. Alternatively, the inserted sequences can be placed at any position in the vector. The term "operably linked" is used to describe a linkage between a nucleic acid sequence and a promoter and/or other regulatory or processing sequences such that the transcription of the nucleic acid sequence is directed by an operably linked promoter sequence, the translation of the sequence is directed by an operably linked translational regulatory sequence, and the post-translational processing of the sequence is directed by an operably linked processing sequence.

Standard techniques for the construction of the vectors of the present invention are well known to those of ordinary skill in the art and can be found in such references as Sambrook et al., *Molecular Cloning: A Laboratory Manual* (Cold Spring Harbor, N.Y., 1989). A variety of strategies are available for ligating fragments of DNA, the choice of which depends on the nature of the termini of the DNA fragments and which choices can be readily made by the skilled artisan.

In one embodiment of the present invention, a recombinant lentiviral expression system comprises three vectors. The first vector comprises a nucleic acid sequence of at least part of the EIAV genome, wherein the vector (i) contains at least one defect in at least one gene encoding an EIAV structural protein, and (ii) contains a defective packaging signal. The second vector comprises a nucleic acid sequence of at least part of the EIAV genome, wherein the vector (i) contains a competent packaging signal, and (ii) contains a multiple cloning site wherein a heterologous gene may be inserted. The third vector comprises a nucleic acid sequence of a virus, wherein the vector (i) expresses a viral envelope protein, and (ii) contains a defective packaging signal.

In another embodiment of the invention, the first vector is a gag/pol expression vector. Gag/pol expression vectors express EIAV proteins required for assembly and release of viral particles from cells, and include the genes encoding viral polyproteins Gag and Gag-Pol. The first vector can also express genes encoding the accessory proteins Rev and Tat. The open reading frame S2, encoding a protein whose function is unknown, can additionally be included in the first vector. The first vector is constructed to contain mutations that exclude retroviral-mediated transfer of viral genes. Such mutations can be in the form of a deletion of sequences in the viral env gene, thus excluding the possibility of generating replication-competent EIAV, or may be deletions of certain cis-acting sequence elements at the 3' end of the genome required for viral reverse transcription and integration. Accordingly, even if viral genes from this construct are packaged into viral particles, they will not be replicated and replication-competent wild-type viruses will not be generated.

In an additional embodiment, the first vector of the expression system is the plasmid pEV53B, which is a 11874 bp plasmid and cDNA clone, which at base pairs 209-863 contains a CMV immediate early enhancer/promoter region located upstream from the EIAV major splice donor site (bp 915-916), the gag coding region (bp 920-2380), the pol coding region (bp 2137-5578) and the ORF S2 coding region (bp 5741-5938). The vector also contains a partial env coding region (bp 5767-7437) and rev coding regions (bp 5892-5992 and 6954-7358). A known Rev Responsive Element (RRE) is contained within the first coding region of rev (bp 5892-5992). The vector does not express a functional tat gene owing to deletion of the first exon of tat, however, the second exon of tat is present at bp 5590-5730. The bovine growth hormone (BGH) polyadenylation signal is provided (bp 7463-7677), as is a phage f1 region (bp 7741-8154), a SV40 early promoter region and origin of replication (bp 8218-8543), a neomycin resistance-coding region (bp 9389-9628), a SV40 polyadenylation signal (bp 9389-9628), a Col E1 origin of replication (bp 10060-10733), and a β-lactamase (ampicillin resistance) coding region (bp 10878-11739).

The second vector of the expression system of the present invention is designed to serve as the vector for nucleic acid transfer, and contains all cis-acting sequence elements required to support encapsidation and reverse transcription (replication) of the vector nucleic acid, as well as a multiple cloning site for insertion of cDNAs encoding heterologous nucleic acid(s). In the present invention, the vector comprising the heterologous nucleic acid is a recombinant EIAV-derived vector that carries the genetic information to be transduced into a target cell, along with cis-acting sequence elements necessary for the packaging and integration of the viral genome. The second vector can contain some portion of the gag coding sequence, as it is believed that certain parts of the gag sequence play a role in the packaging of the EIAV genome. The second vector can also contain the so-called lentiviral 'DNA flap' region that is a cis-acting sequence derived from lentiviral DNA and contains a central polypurine tract (cPPT) and central termination site (CTS) sequence involved in reverse transcription. Additionally, the second vector can contain cis-acting elements to promote efficient export of newly synthesized RNA from the nucleus to the cytoplasm. Examples of RNA export signals include the homologous lentiviral Rev Responsive Element (RRE), which works in concert with Rev, and the heterologous woodchuck hepatitis virus post-transcriptional regulatory element (WPRE), which may also increase gene expression by RNA stabilization or other means. In addition, the 5' splice donor site contained in the LTR can contain a mutation that increases the titer of the produced virus, as described in, e.g., Tan et al., *J. Virol.* 70:3645-3658 (1996).

An example of a second vector of this invention is the plasmid pESIN6.1CpuroW, a 6866 bp plasmid derived from EIAV that expresses the *Streptomyces alboniger* puromycin reporter gene. The plasmid contains two CMV immediate-early enhancer promoter regions (located at bp 1-734 and 1863-2384); R-U5 sequence domains from the EIAV long terminal repeat (LTR) (bp 735-857); a leader sequence containing the EIAV RNA encapsidation signal (~bp 870-1200), a mutated tat translation start site (CTG to TAG at bp 909-911), a splice donor site at bp 996-997, a mutated gag translation start site (ATG to TAG at bp 1000-1003, a partial EIAV gag sequence (bp 1004-1200); a 'DNA flap' sequence containing the EIAV central polypurine tract (cPPT, bp 1314-1330) and central termination site (CTS) sequence (bp 1422-1448); a viral splice acceptor sequence (bp 1753-1754), a Rev Responsive Element (RRE, bp 1755-1857); a puromycin coding sequence (bp 2480-3105); a woodchuck hepatitis virus post-transcriptional regulatory element (bp 3110-3996); an EIAV Self-Inactivating (SIN) LTR sequence deleted of EIAV enhancer/promoter sequences (bp 4037-4183); a phage f1 region (bp 4280-4735); an ampicillin resistance coding region (bp 5174-6034); and a ColE1 origin of replication (bp 5554-6228).

As will be appreciated by one skilled in the art, the nucleotide sequence of the heterologous nucleic acid can be of any nucleotide sequence. For example, the heterologous nucleic acid can be a reporter gene sequence or a selectable marker gene sequence. A reporter gene sequence, as used herein, is any gene sequence which, when expressed, results in the production of a protein whose presence or activity can be monitored. Examples of suitable reporter genes include the gene for galactokinase, β-galactosidase, chloramphenicol acetyltransferase, β-lactamase, etc. Alternatively, the reporter gene sequence can be any gene sequence whose expression produces a gene product that affects cell physiology in some detectable way.

A selectable marker gene sequence is any gene sequence capable of being expressed to produce a protein, the presence of which permits one to selectively propagate a cell that contains it. Examples of selectable marker genes include gene sequences capable of conferring host resistance to antibiotics (e.g., puromycin, ampicillin, tetracycline, kanamycin, and the like), of conferring host resistance to amino acid analogues, and/or of permitting the growth of bacteria on additional carbon sources or under otherwise impermissible culture conditions. A gene sequence can be both a reporter gene and a selectable marker gene sequence. Examples of reporter genes of the present invention are the lacZ gene that encodes the β-galactosidase activity of *E. Coli*; and the gene encoding puromycin resistance.

Reporter or selectable marker gene sequences of this invention are those that are sufficient to permit the recognition or selection of the vector in normal cells. In one embodiment of the invention, the reporter gene sequence will encode an enzyme or other protein which is normally absent from mammalian cells, and whose presence can, therefore, definitively establish the presence of the vector in such a cell.

The heterologous nucleic acid of this invention can also comprise the coding sequence of a desired product such as a suitable biologically active protein or polypeptide, immunogenic or antigenic protein or polypeptide, or a therapeutically active protein or polypeptide. Alternatively, the heterologous nucleic acid can comprise a sequence complementary to an RNA sequence, such as an antisense RNA sequence, which antisense sequence can be administered to a subject to inhibit expression of a complementary polynucleotide in the cells of the subject.

Expression of the heterologous nucleic acid can provide immunogenic and/or antigenic protein(s) and/or polypeptide(s) to achieve an immune response, which can include an antibody response. Such antibodies can be effective in imparting a therapeutic effect in a subject in the context of a vaccination and/or the antibodies can be collected from an animal in a body fluid such as blood, serum or ascites.

In a further embodiment of the present invention, the third vector comprises a nucleic acid that encodes a viral envelope protein. Such a vector will accordingly comprise a nucleic acid sequence encoding a viral protein under the control of a suitable promoter. The viral envelope protein can be a lentivirus envelope protein. However, it is possible to alter the host range of cells that the viral vectors of the present invention can infect by utilizing an envelope gene from another virus. In other words, it is possible to expand the host range of the EIAV vectors of the present invention by taking advantage of the capacity of the envelope proteins of certain viruses to participate in the encapsidation of other viruses. The G-protein of vesicular-stomatitis virus (VSV-G; see, e.g., Rose and Gillione, *J. Virol.* 39:519-528 (1981); Rose and Bergmann, *Cell* 30:753-762 (1982)) efficiently forms pseudotyped virions with genome and matrix components of other viruses. These VSV-G pseudotyped vectors have a very broad host range and can be concentrated to high titers by ultracentrifugation. As used herein, the term "pseudotype" refers to a viral particle that contains nucleic acid of one virus but the envelope protein of another virus.

An example of a third vector of the present invention is the plasmid and cDNA clone pCI-VSV-G, an expression vector for the envelope glycoprotein VSV-G. The plasmid contains 5679 base pairs and includes the CMV immediate-early enhancer promoter region (bp 1-795), a chimeric intron region (bp 857-989), the VSV-G coding region (bp 1088-2633), a phage f1 region (3093-3548), a SV40 late polyadenylation signal (bp 2782-3003), a ColE1 origin of DNA replication (bp 4992-5666) and an ampicillin resistance coding region (bp 3987-4847).

In a method of the present invention, infectious, replication-defective EIAV particles can be prepared according to the methods disclosed herein in combination with techniques known to those skilled in the art. The method includes transfecting a lentivirus-permissive cell with the vectors of the present invention; producing the EIAV-derived particles in the transfected cell; and collecting the virus particles from the cell. The step of transfecting the lentivirus-permissive cell can be carried out according to any suitable means known to those skilled in the art. For example, in a method of the present invention, the three-plasmid expression system described herein is used to generate EIAV-derived retroviral vector particles by transient transfection. As another example, uptake of the vectors into the cells can be achieved by any suitable means, such as for example, by treating the cells with DEAE-dextran, treating vector-derived DNA or RNA with LIPOFECTIN® before addition to the cells, or by electroporation. These techniques are well known in the art.

The step of facilitating the production of the infectious viral particles in the cells is carried out using conventional techniques, such as by standard cell culture growth techniques that are well known in the art.

The step of collecting the infectious virus particles is also carried out using conventional techniques. For example, the infectious particles can be collected by cell lysis, or collection of the supernatant of the cell culture, as is known in the art. Optionally, the collected virus particles can be purified if desired. Suitable purification techniques are well known to those skilled in the art.

If desired by the skilled artisan, lentiviral stock solutions can be prepared using the vectors and methods of the present invention. Methods of preparing viral stock solutions are known in the art and are illustrated by, e.g., Soneoka et al., *Nucl. Acids Res.* 23:628-633 (1995) and Landau et al., *J. Virol.* 66:5110-5113 (1992). In a method of producing a stock solution in the present invention, lentiviral-permissive cells of this invention are transfected with the vectors of the present invention. The cells are then grown under suitable cell culture conditions, and the lentiviral particles are collected from either the cells themselves or from the cell media, as described above.

The vectors of the present invention are also useful in preparing packaging cells (i.e., cells that express EIAV virus proteins, which cells, by themselves, cannot generate infectious virus particles). Methods for preparing packaging cells that express retrovirus proteins are known in the art and are exemplified by the methods set forth in, for example, U.S. Pat. No. 4,650,764 to Temin et al., which reference is incorporated herein in its entirety for the teachings of these methods. A packaging cell of the present invention can comprise a lentivirus-permissive cell of this invention, comprising an EIAV nucleic acid encoding at least one EIAV structural protein, which nucleic acid is packaging-signal defective, thus rendering the cell itself capable of producing at least one EIAV structural protein, but not capable of producing replication-competent infectious virus. The packaging cell can then have other nucleic acid sequences introduced (e.g., pESIN6.1CpuroW and/or pCI-VSV-G), which can contain heterologous nucleic acid(s) and an appropriate packaging signal. Once transfected with the additional sequence or sequences, the packaging cell is used to produce stocks of EIAV viruses that contain heterologous nucleic acid, but which viruses are themselves replication-incompetent.

The present invention is more particularly described in the following examples, which are intended as illustrative only since numerous modifications and variations therein will be apparent to those skilled in the art.

EXAMPLES

Example 1

Cells

HEK 293 cells were obtained from the American Type Culture Collection (ATCC). A library of clones of these cells was prepared by limiting dilution and screened for cell lines that showed the greatest ability for producing retroviral and lentiviral vectors (Johnson et al. "Effect of host modification and age on airway epithelial gene transfer mediated by a murine leukemia virus-derived vector" *J. Virol.* 72:8861-72 (1998)). One of these clones, 293.101, was chosen for constructing EIAV helper cell lines and EIAV vector packaging cells. The B-241 cell line is an ETAV vector helper cell line. These cells were derived from 293.101 cells by stable transfection with an expression vector (EV53B) that expresses the EIAV gag, pol, S2, and rev genes from a CMV promoter. The BiG-45 cell line is an EIAV packaging cell line. These cells were derived from B-241 cells by stable transfection with a plasmid expression vector encoding a tetracycline regulatable VSV-G envelope cDNA and a CMV promoter driven tetracycline repressor gene. BiG-45/8Z-20 cells were derived from stable transfection of BiG-45 cells with pONY8Z, an EIAV gene transfer vector encoding a bacterial lacZ reporter gene (Rohll et al. "Design, production, safety, evaluation, and clinical applications of nonprimate lentiviral vectors" *Methods Enzymol* 346:466-500 (2002)).

Integrin Expression Plasmids

The pCXIH expression vector was used to express the human $\alpha_{IIb}$ or $\alpha_v$ integrin subunits. The pCXIP expression vector was used to express the wild type or mutated human $\beta_3$ integrin subunit. These vectors use the CMV promoter to drive expression of the inserted cDNA and contain an IRES sequence linked to either a hygromycin resistance gene (pCXIH) or a puromycin resistance gene (pCXIP) for selection in animal cells.

The pCXIP plasmid is 5562 bp in length and is a bicistronic expression vector designed to express a target gene along with the puromycin selectable marker. This vector contains a CMV immediate-early enhancer/promoter region (bp 1-532), a multiple cloning site region for inserting the sequence to be expressed (bp 639-687), an internal ribosome entry site sequence (bp 689-1261), a puromycin resistance gene (bp 1298-1894), a poly A addition signal from murine leukemia virus (bp 2268-2693), a SV40 origin of DNA replication (bp 2973-3259), a Col E1 origin of DNA replication region (bp 3580-4200), and an Ampicillin resistance gene (bp 4340-5200).

The pCXIH plasmid is 6161 bp in length and is a bicistronic expression vector designed to express a target gene along with the hygromycin selectable marker. This vector contains a CMV immediate-early enhancer/promoter region (bp 1-532), a multiple cloning site region for inserting the sequence to be expressed (bp 640-680), an internal ribosome entry site sequence (bp 689-1263), a hygromycin resistance gene (bp 1287-2321), a poly A addition signal from murine leukemia virus (bp 2867-3292), a SV40 origin of DNA replication (bp 3572-3858), a Col E1 origin of DNA replication region (bp 4179-4799), and an Ampicillin resistance gene (bp 4939-5799).

For expression of both $\alpha_v$ and $\beta_3$ integrin subunits in BiG-45 cells, the pVITRO2-mcs expression vector (InvivoGen, San Diego) was used. This vector uses a composite human ferritin heavy chain promoter/SV40 enhancer sequence to drive expression of human $\alpha_v$ integrin and a composite human ferritin light chain promoter/CMV enhancer sequence to drive expression of human $\beta_3$ integrin.

Expression of Integrin Subunits in 293-Based EIAV Producer Cells

Figure 2:
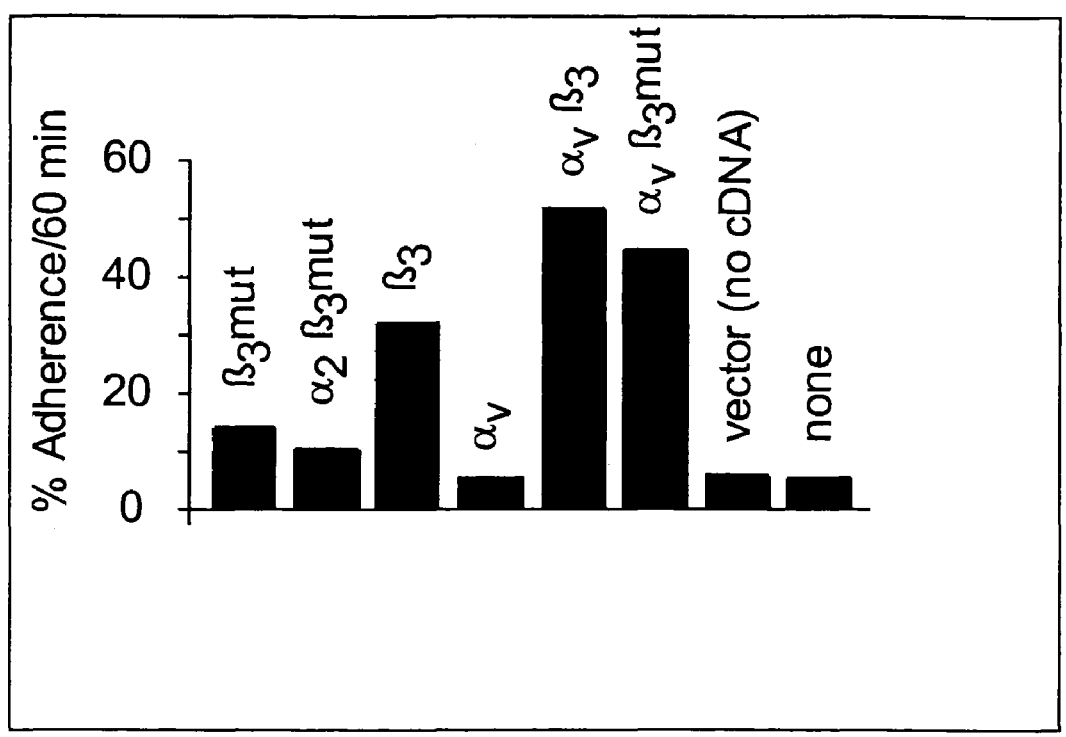
FIG. 2. Increased adherence of BiG-45 packaging cells after transfection with human integrins. BiG-45 EIAV packaging cells containing an equine infectious anemia virus (EIAV)-green fluorescent protein (GFP) vector were transfected with various human integrin cDNAs. Cells were seeded into wells of a regular tissue culture plate. One hour after seeding, the GFP fluorescence of each well was determined before and after gentle washing to determine the percentage of cells adhering to the plate. A Cytofluor plate reader was used to measure fluorescence.

Integrin cDNAs encoding $\alpha_{IIb}$, $\alpha_v$ and $\beta_3$ subunits were subcloned into expression vectors using the CMV promoter and various combinations were stably transfected into the B-241 EIAV helper cell line to generate a series of cell lines. After 12 days of drug selection, the cell colonies resulting from each transfection were pooled and analyzed for cell surface expression of the individual integrin subunits $\alpha_{IIb}$, $\alpha_v$ and $\beta_3$ or as integrin receptors $\alpha_{IIb}\beta_3$, or $\alpha_v\beta_3$ by immunofluorescence of live cells by flow cytometry (FIG. 1). It was found that each integrin was expressed at the cell surface of B-241 cells. The expression of both the $\alpha$ and $\beta$ subunits together enhanced their overall expression at the cell surface as compared to expressing individual subunits. Immunofluorescence studies confirmed that expression of each integrin was greatly enhanced relative to endogenous integrin expression Attachment of Integrin-Modified 293 Cells to Tissue Culture Substrate A cell attachment assay was used to test whether expression of $\beta_3$ integrin subunit alone or together with its $\alpha_{IIb}$ or $\alpha_v$ binding partner would result in increased adherence to tissue culture substrate. The assay involved transiently expressing the integrin sub-units in 293 based BiG-45 EIAV packaging cells expressing green fluorescent protein. The cells were plated at $3 \times 10^5$ cells per well in 12-well plates. The plating efficiency of the cells was determined 1 hr post-plating by measuring the fluorescence of the cells before and after washing the cells. Overexpression of the $\beta_3$ integrin subunit alone resulted in a significant increase in adhesion of the 293 cells to untreated tissue culture plates as compared to unmodified cells (FIG. 2). Co-expression of $\alpha_v$ further increased 293-cell adherence. A mutant form of the $\beta_3$ sub-unit was also tested, which when associated with $\alpha_{IIb}$ on platelets causes the $\alpha_{IIb}\beta_3$ receptor to be permanently activated. The mutant $\beta_3$ sub-unit did not provide any increase in cell adhesion alone or in association with $\alpha_{IIb}$ or $\alpha_v$ as compared to wild type $\beta_3$ sub-unit (FIG. 2). Thus, expression of the wild-type human $\alpha_v\beta_3$ integrin receptor in 293-derived cells significantly increases their ability to attach to regular tissue culture plates.

Effect of Integrin Modification upon Roller Bottle Culture of 293 Cells

Figure 3:
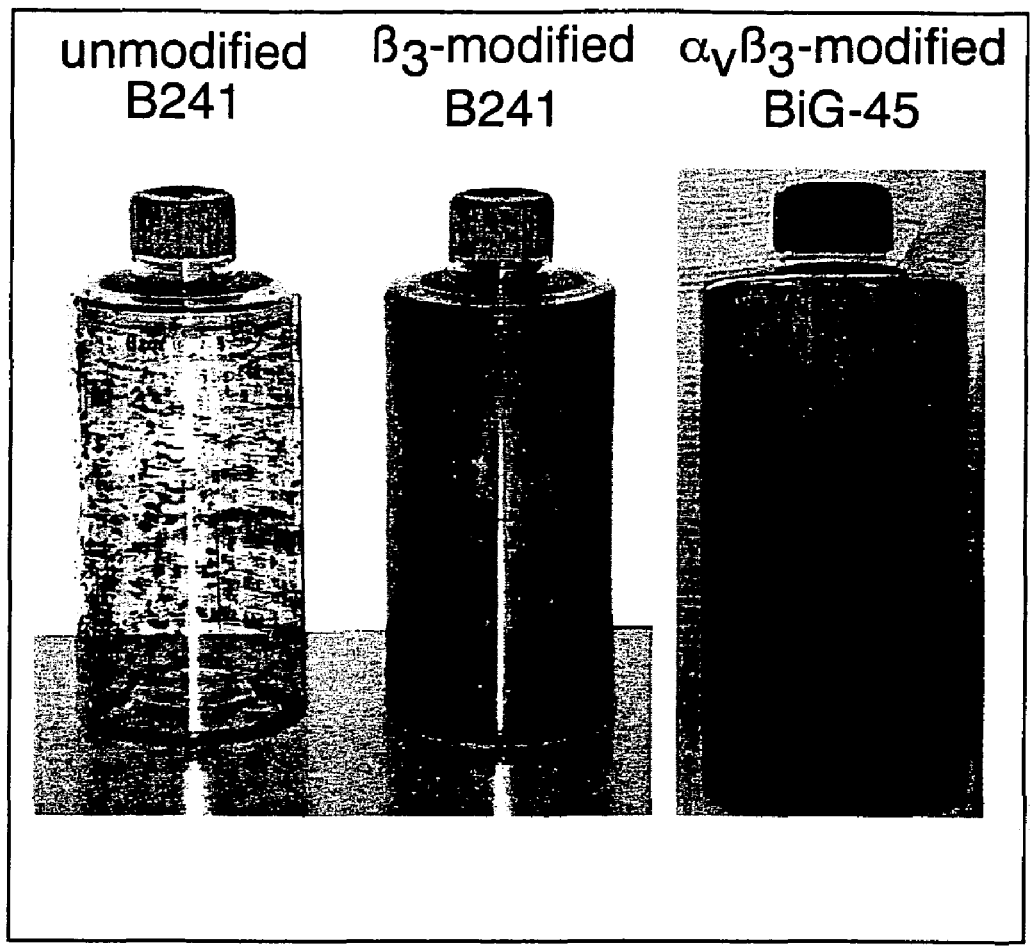
FIG. 3. Roller bottle culture of EIAV vector producer cell lines with and without modification with human integrin cDNAs. Each bottle was seeded with $7.75\times10^7$ cells.
Figure 4:
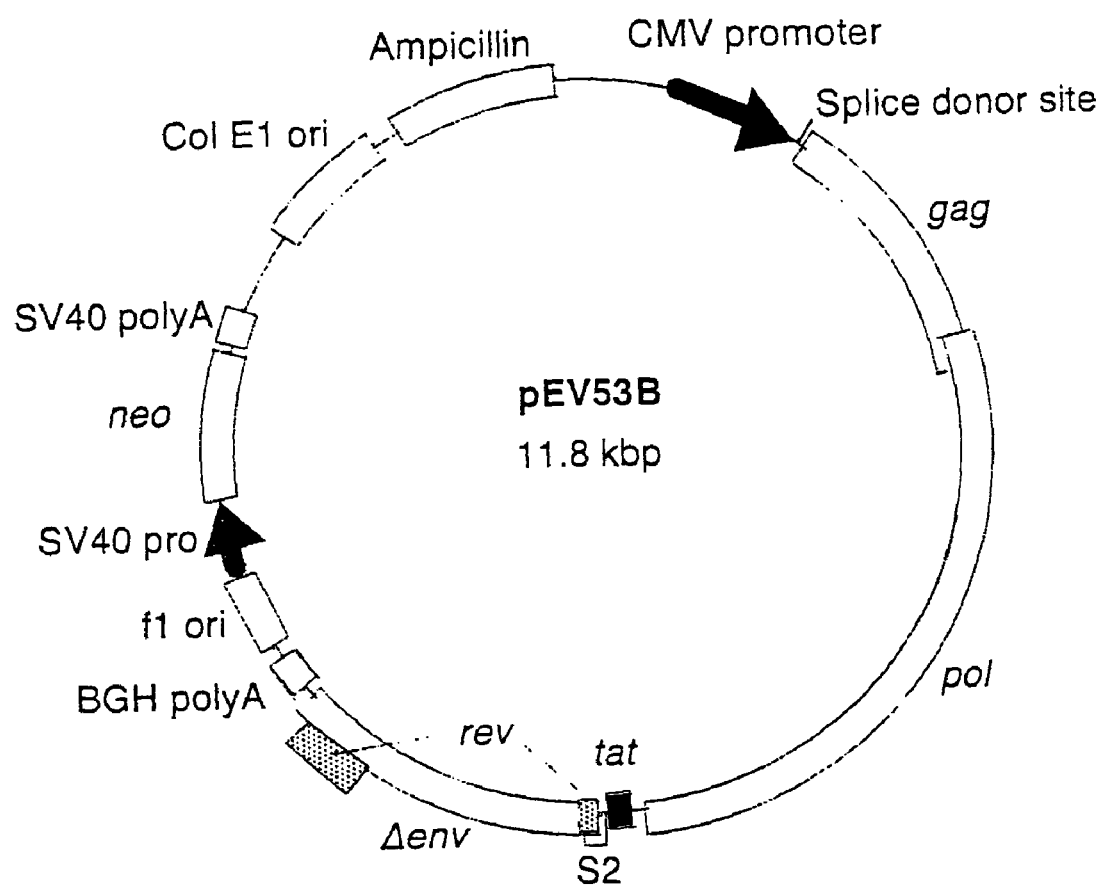
FIG. 4. Plasmid pEV53B.
Figure 5:
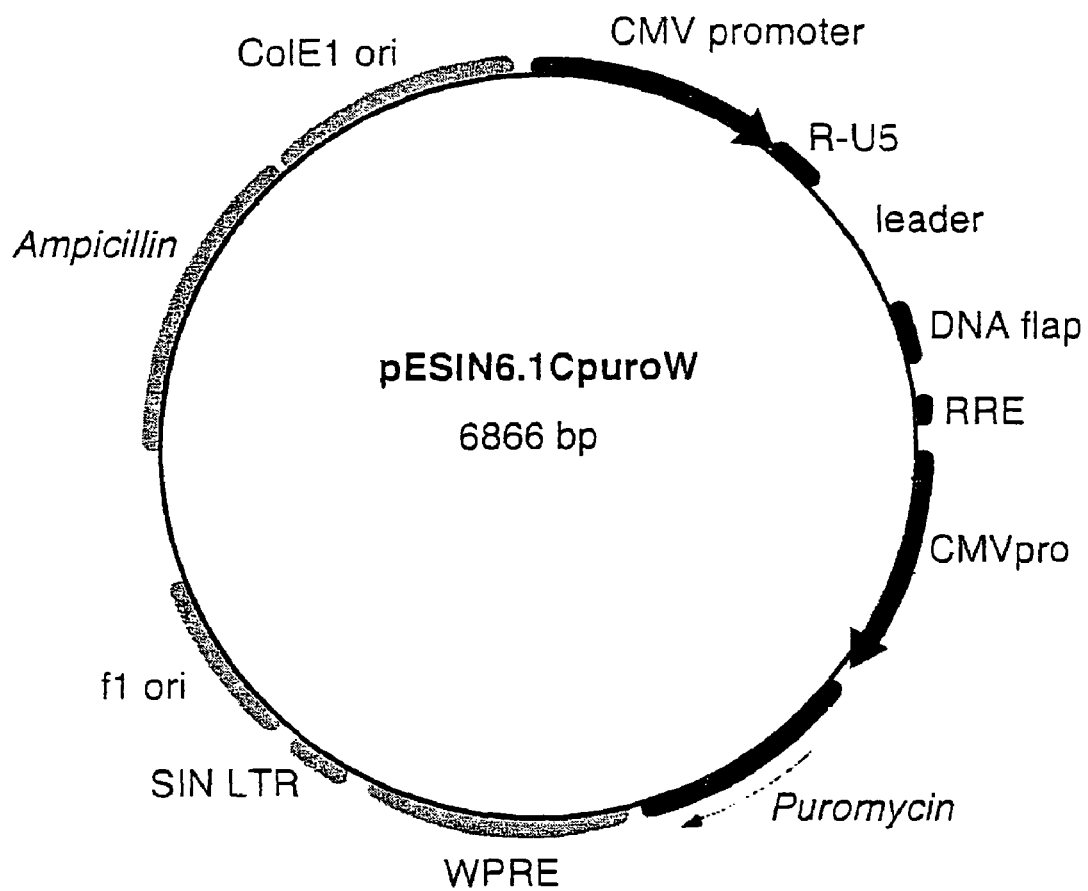
FIG. 5. Plasmid pESIN6.1CpuroW.
Figure 6:
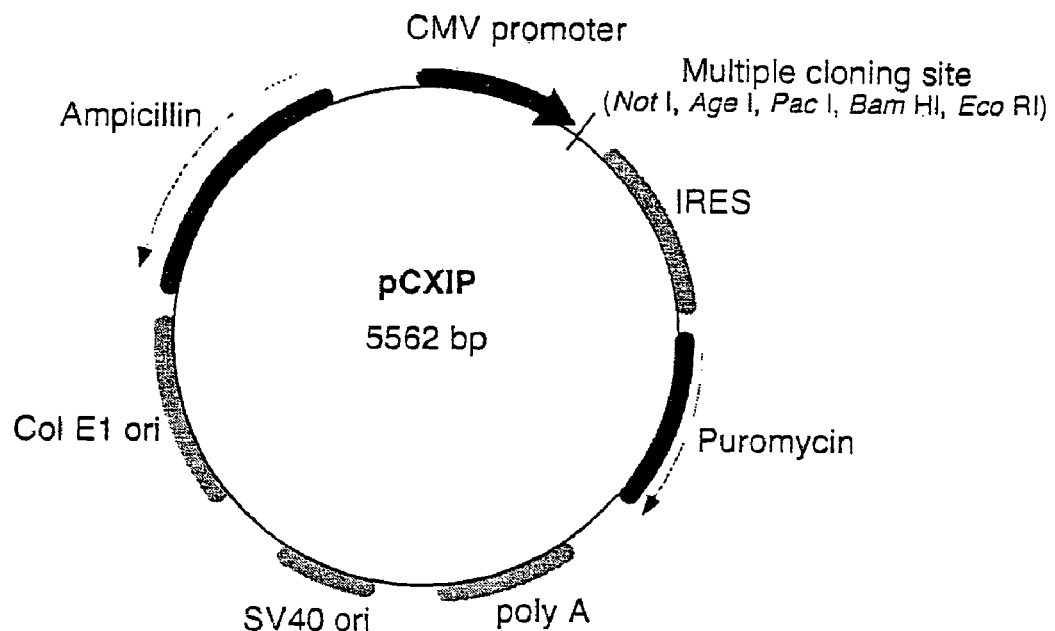
FIG. 6. Plasmids pCXIP and pCXIH.
Figure 6:
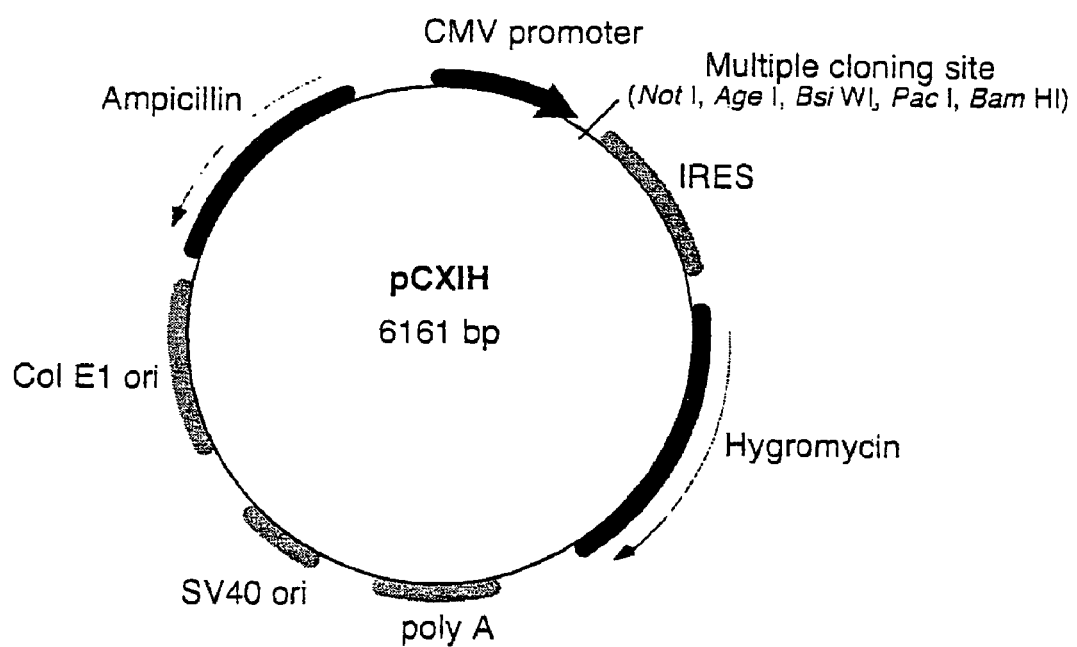
Figure 7:
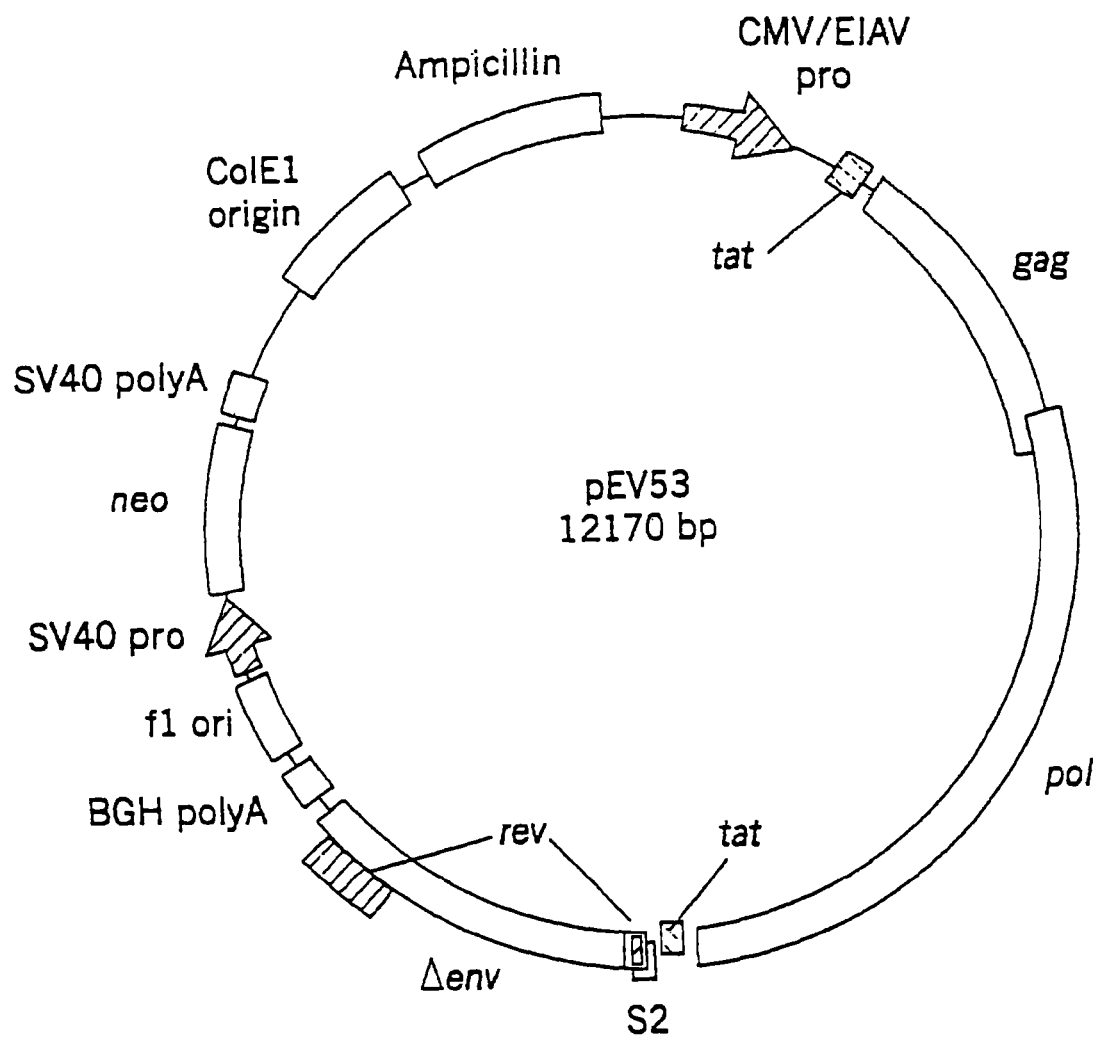
FIG. 7. Plasmid pEV53.
Figure 8:
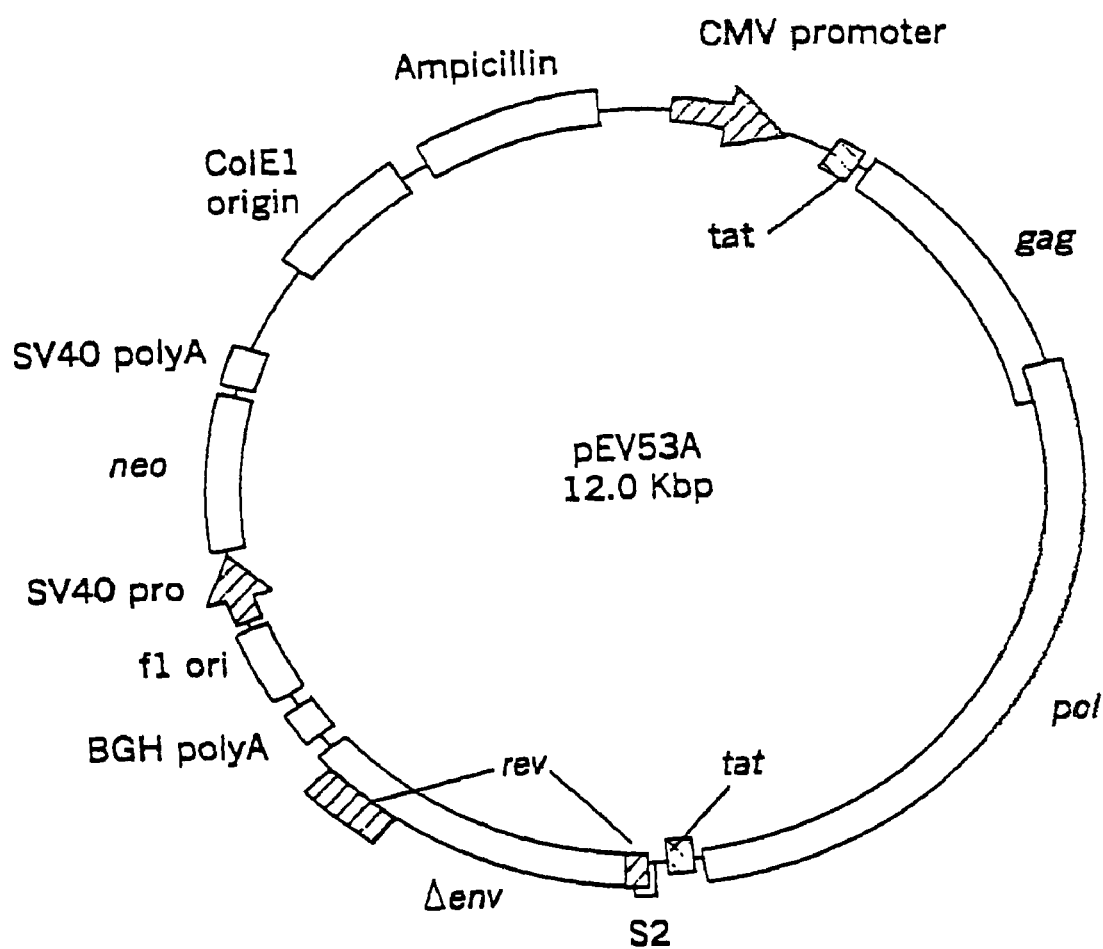
FIG. 8. Plasmid pEV53A.
Figure 9:
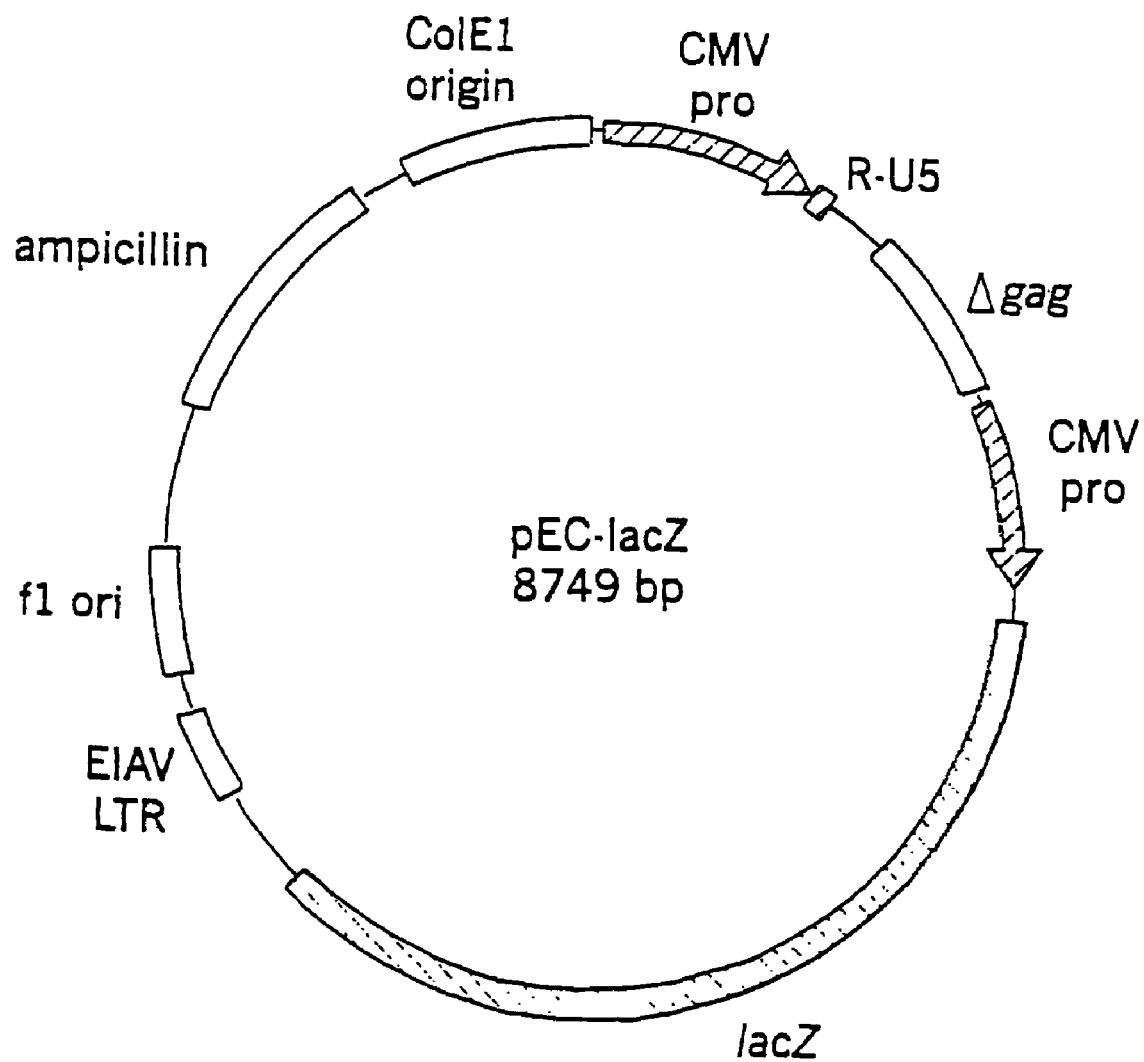
FIG. 9. Plasmid pEC-lacZ.
Figure 10:
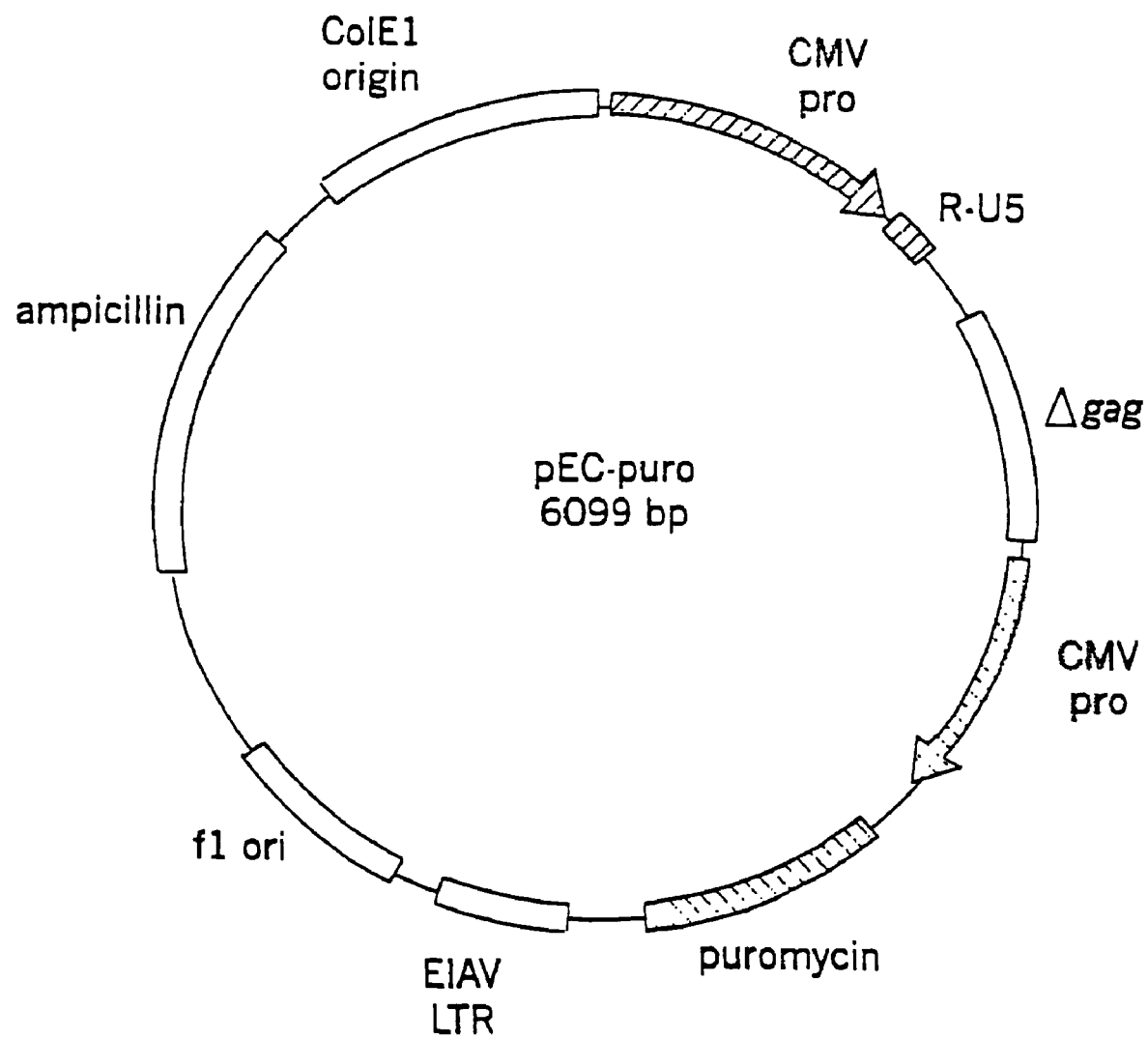
FIG. 10. Plasmid pEC-puro.
Figure 11:
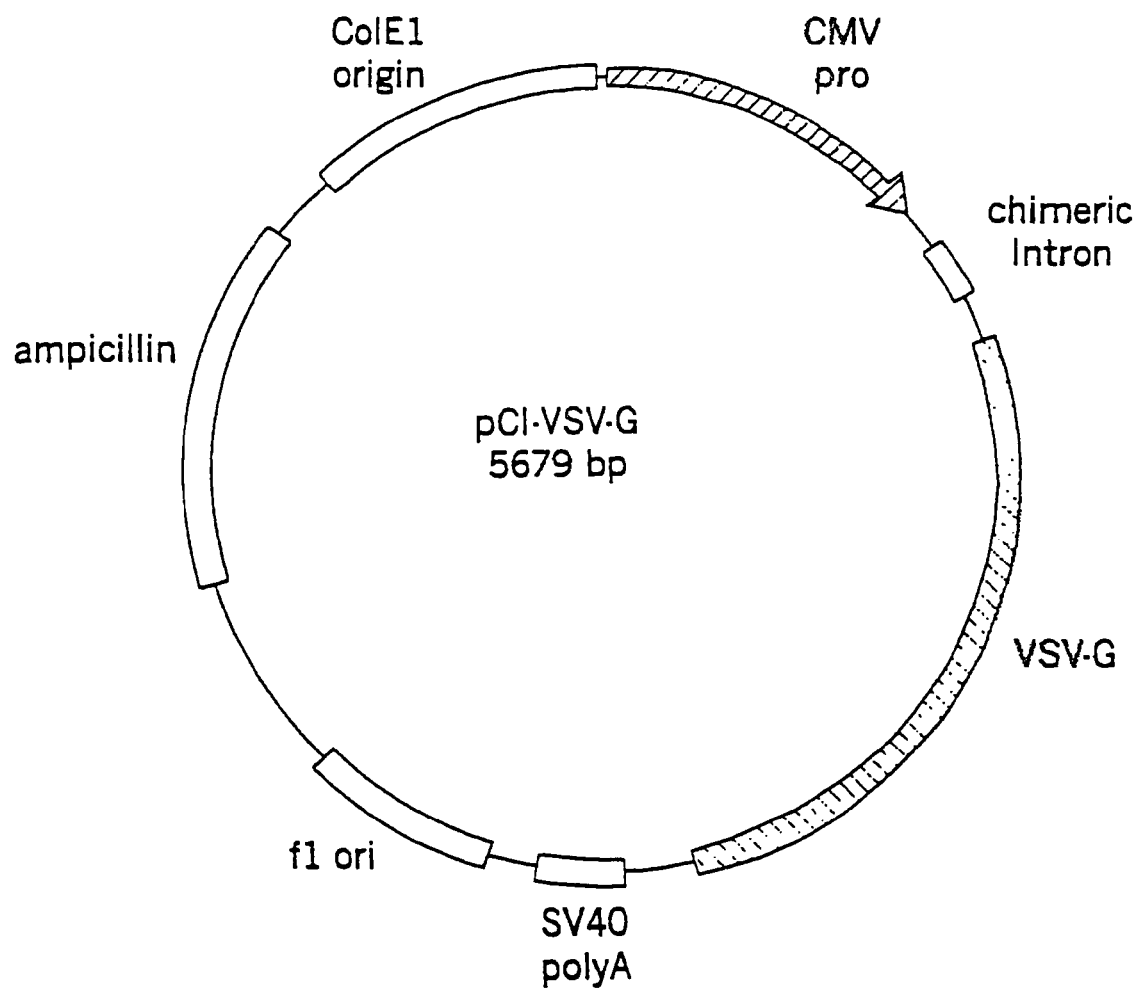
FIG. 11. Plasmid pCI-VSV-G.

To reduce the time and effort required to produce lentiviral vectors, the ability of integrin-modified cells to attach and grow in roller bottle culture was investigated. In an initial experiment, integrin $\beta_3$ modified B-241 cells or unmodified B-241 cells were seeded into roller bottles. The next day, cells were stained with crystal violet and photographed (FIG. 3). The $\beta_3$ modified cells adhered significantly better than unmodified cells, although some clumping of cells was evident. To test the effect of expressing $\beta_3$ along with its $\alpha_v$ binding partner, BiG-45 packaging cells producing an EIAV-lacZ vector (BiG-45/8Z-20) were stably transfected with the pVITRO2mcs vector expressing both integrins and seeded into rollers bottles. One day after seeding, the cells were stained for expression of the lacZ gene with X-Gal. As shown in FIG. 3, the cells showed a more uniform attachment with less cell clumping than cells modified with $\beta_3$ alone. In subsequent experiments, the plating efficiency of integrin-modified and unmodified B-241 cells was determined 24 hr after seeding into roller bottles. For both $\beta_3$ and $\alpha_v\beta_3$ modified B-241 cells, the plating efficiency was 98.3%±1.5% (n=6). By contrast, for unmodified B-241 cells, the plating efficiency was only 45.7%±15.3% (n=3).

Effect of Integrin Expression on Lentiviral Vector Production

The effect of integrin expression on EIAV vector production in a transient vector production system using calcium phosphate-mediated transfection was determined by co-transfecting an EIAV vector (ESIN6.1CpuroW) encoding a puromycin gene along with a vector encoding the VSV-G envelope into the B-241 helper cell line. It was found that expression of $\alpha_{IIb}$ or $\alpha_v$ integrin subunits alone had no effect on vector titers (Table 1). Co-expression of $\alpha_{IIb}$ with $\beta_3$ consistently resulted in a 4-5 fold decrease in vector titers. In contrast, expression of $\beta_3$ alone or in combination with $\alpha_v$ integrin resulted in a 30-60% increase in vector production.

Modification of B-241 cells, or other 293-based cell lines, with $\alpha_v\beta_3$ integrins resulted in a flattening of the cells such that integrin modified cells occupied a greater surface area than unmodified cells. Since optimized transfection protocols typically use cultures that are 80-90% confluent, this resulted in fewer numbers of integrin-modified cells than unmodified cells for transfection experiments. To further characterize EIAV vector production from integrin-modified cells, the yield of infectious vector per cell was determined and compared to unmodified cells. In addition, the effect of agents (glycerol or DMSO) used to increase the efficiency of DNA uptake was determined (Lopata et al. 1984. "High level transient expression of a chloramphenicol acetyl transferase gene by DEAE-dextran mediated DNA transfection coupled with a dimethyl sulfoxide or glycerol shock treatment" *Nucleic Acids Res* 12:5707-17). As shown in Table 2, the yield of vector produced per cell increased 3.6-fold using cells modified with $\alpha_v\beta_3$ integrins. Furthermore, the yield of vector in integrin-modified cells could be further increased approximately 3-fold by incorporating a glycerol or DMSO shock treatment into the protocol to enhance DNA uptake (Table 2). In contrast, vector production from unmodified cultures was not enhanced by treatment with glycerol or DMSO. In part, this was attributed to cell losses due to poor adherence by unmodified cultures. Decreasing the duration of glycerol or DMSO treatment to 30 seconds resulted in decreased cell loss of unmodified cultures, but vector yield was not enhanced.

Example 2

Modification of HEK 293 Cell Integrin Expression Profile Allows Convenient Large-Scale Roller Bottle Production of Lentiviral Vectors EIAV and HIV Based Lentiviral Vector Production Using Roller Bottles The possibility that large-scale high-titer vector production could be accomplished using roller bottle culture of integrin-modified 293 cells was investigated. In these studies, various methods were tested for producing lentiviral vectors using roller bottles. Some examples are shown in Table 3. In one example, roller bottle cultures of $\alpha_v\beta_3$-modified B-241 helper cells, stably expressing an EIAV gag-pol gene, were co-transfected with an EIAV vector (ESIN6.1CpuroW) encoding a puromycin resistance gene and a VSV-G envelope gene. After a 1000-fold concentration, a vector preparation with a titer of $1.2 \times 10^9$ infectious units/ml was obtained. This level of vector production compares favorably with levels of vector production produced by unmodified cells grown in tissue culture plates (Table 1).

In a second example, a BiG-45 EIAV packaging cell line stably transfected with an EIAV lacZ gene was induced to produce virus that had a titer of $2 \times 10^9$ after concentration. A third example shows that the procedure can be scaled up to produce vector in quantities suitable for animal studies. In this case, the goal was to produce quantities of vector ($>3 \times 10^9$ total infectious units) required for ex-vivo gene transfer to canine hematopoietic stem cells. A three-plasmid transfection of 12 roller bottles containing $\alpha_v\beta_3$-modified 293T cells was performed to produce an HIV-1 vector. Vector (90 ml/roller bottle) was harvested on three successive days beginning at 48 hr post-transfection. A total of 3240 ml was harvested and concentrated approximately 550-fold to 6 ml. The total yield was $1.4 \times 10^{10}$ infectious vector particles, more than sufficient to carry out the animal studies.

Human embryonic kidney cells (HEK 293) are the most widely used cell type for production of viral gene transfer vectors. They are highly transfectable with plasmid DNAs encoding viral proteins using a number of transfection reagents and protocols to transiently express recombinant viruses. A variety of stable 293-based packaging cell lines have also been generated for virus production. A gene transfer system based on the non-primate lentivirus equine infectious anemia virus (EIAV) was developed, which utilizes a stable 293 cell-based inducible packaging cell line (BiG 45) for high-titer virus production. Large-scale production of vectors using 293 cells is often difficult since they easily detach from regular tissue culture plates. This can be overcome by adapting the cells to grow in suspension cultures, however this can result in a significant loss in viral titer. Alternately, cultures can be grown in vessels that are treated with cell attachment substrates such as fibronectin or poly-lysine. Both strategies, however, significantly increase the cost of large-scale vector production.

In this study, a new strategy for increasing the adhesion properties of 293 cells by modifying their integrin expression profile was tested. First tested were the effects of over-expressing the integrin $\beta_3$ subunit alone or in combination with its known binding partners, $\alpha_v$ or $\alpha_{IIb}$. The cell adhesion assay involved transiently expressing integrin sub-units in 293-based EIAV packaging cells expressing green fluorescent protein. The cells were plated at a density of $2$-$4 \times 10^5$ cells/well on untreated multi-well plates. The plating efficiency of the cells was determined 1 hr after plating by measuring the fluorescence of the cells before and after washing the cells. It was observed that over-expression of the $\beta_3$ integrin subunit in 293 cells resulted in a significant increase in adhesion of the cells to untreated tissue culture plates as compared to unmodified cells. Co-expression of $\alpha_v$, but not $\alpha_{IIb}$ further increased 293 cell adherence. Production of both HIV and EIAV-based lentiviral vectors from integrin-modified 293 cells was also investigated. Vector titers and reporter gene expression in target cells were not compromised as a result of this modification and this led to a scale up of vector production in roller bottles for generating vectors for in vivo experiments.

In summary, over-expression of $\alpha_v$ and $\beta_3$ in 293 cells increases adhesion to regular untreated tissue culture dishes without compromising viral vector production.

The foregoing is considered as illustrative only of the principles of the invention. Further, since numerous modifications and changes will readily occur to those skilled in the art, it is not desired to limit the invention to the exact construction and operation shown and described herein. Therefore, accordingly, all suitable modifications and equivalents fall within the scope of the invention.

All publications, patent applications, patents and other references cited herein are incorporated by reference in their entireties for the teachings relevant to the sentence and/or paragraph in which the reference is presented.

TABLE 1

Effect of Integrin Expression on EIAV Vector Production

| Integrin cDNA added[1] | Titer[2] | Relative titer[3] |
|---|---|---|
| none | $8.5 \times 10^5$ | 1.0 |
| $\alpha_{IIb}$ | $7.7 \times 10^5$ | 0.9 |
| $\alpha_v$ | $7.9 \times 10^5$ | 0.9 |
| $\beta_3$ | $1.1 \times 10^6$ | 1.3 |
| $\alpha_{IIb}\beta_3$ | $2.1 \times 10^5$ | 0.2 |
| $\alpha_v\beta_3$ | $1.4 \times 10^6$ | 1.6 |

[1]B-241 cells were modified with expression vectors containing cDNAs for the indicated human integrin.
[2]Cells were co-transfected with an EIAV vector plasmid encoding puromycin resistance and a VSV-G envelope expression vector. The titer of virus produced 48 hr after transfection is given as puromycin resistant colonies per ml un-concentrated tissue culture supernatant.
[3]Titer relative to cells with no modification.

TABLE 2

Effect of Integrin Expression on EIAV Vector Production Per Cell

| Integrin cDNA added[1] | Vector yield (infectious units) per cell[2] | | |
|---|---|---|---|
| | CaPO$_4$ | CaPO$_4$ with Glycerol Shock[3] | CaPO$_4$ with DMSO Shock[4] |
| none | 1.0 | 1.4 | 1.2 |
| $\alpha_v\beta_3$ | 3.6 | 13.3 | 12.0 |

[1]B-241 cells were modified with expression vectors encoding cDNAs for $\alpha_v\beta_3$ human integrins.
[2]Unmodified cells ($1 \times 10^6$ per 35-mm well of a 6-well plate) or $\alpha_v\beta_3$ integrin-modified cells ($4.5 \times 10^5$ per 35-mm well of a 6-well plate) were plated at 80% confluency and co-transfected with an EIAV vector plasmid encoding puromycin resistance and a VSV-G envelope expression vector. The total yield of vector (in 2 ml tissue culture supernatant) produced 48 hr after transfection is given as puromycin resistant colonies (infectious units) of vector per cell. The results represent the average of two independent experiments.
[3]Four hours after adding the CaPO$_4$-DNA transfection mixture, the medium was removed and cultures were washed once with 5 ml phosphate-buffered saline (PBS). The cells were treated for 2 minutes at room temperature with 15% (v/v) glycerol in HEPES-buffered saline (50 mM HEPES (pH 7.1), 280 mM NaCl and 1.5 mM Na$_2$HPO$_4$). The glycerol solution was removed and cultures were washed once with PBS. Regular growth medium was added and the cells were returned to the 37° C incubator.
[4]Four hours after adding the CaPO$_4$-DNA transfection mixture, the medium was removed and cultures were washed once with 5 ml phosphate-buffered saline (PBS). The cells were treated for 2.5 minutes at room temperature with 10% (v/v) DMSO in PBS. The DMSO solution was removed and cultures were washed twice with PBS. Regular growth medium was added and the cells were returned to the 37° C incubator.

TABLE 3

Lentiviral Vector Production in Roller Bottle Culture of Cells Modified with $\alpha_v\beta_3$ Integrins

| Integrin-Modified Cells | Lentiviral Vector Produced[1] | Volume produced (ml) | Final Volume (ml)[2] | Fold conc | Final titer[3] |
|---|---|---|---|---|---|
| B-241($\alpha_v\beta_3$) | SIN6.1CMVpuro (EIAV) | 90 | 0.09 | 1000 | $1.2 \times 10^9$ |
| BiG-45/8Z-20($\alpha_v\beta_3$) | pONY8Z (EIAV) | 180 | 0.12 | 1500 | $2 \times 10^9$ |
| 293T($\alpha_v\beta_3$) | EF1-GFP (HIV) | 3240 | 6 | 550 | $2.4 \times 10^9$ |

[1]Vectors were produced in transfected B-241 cells and 293T cells following 2-plasmid and 3-plasmid transfection, respectively. Vector production from BiG-45/8Z-20 cells, which carry an integrated EIAV lacZ gene transfer vector, was induced by treatment with 10 mM sodium butyrate and 1.5 µg/ml doxycycline.
[2]Viral vector were concentrated by high-speed centrifugation to pellet the virus (100,000 × g-hours at 4° C.) EIAV vector plasmid encoding puromycin resistance and a VSV-G envelope expression vector. The titer of virus produced 48 hr after transfection is given as puromycin resistant colonies per ml tissue culture supernatant.
[3]Vector transducing units/ml.

What is claimed is:

1. A method of producing recombinant lentivirus particles in modified cells in a culture vessel, comprising: introducing into the modified cells, which are modified to comprise a stably integrated recombinant nucleic acid selected from the group consisting of:
   i) a nucleic acid encoding an integrin $\beta_3$ subunit;
   ii) a nucleic acid encoding an integrin $\alpha_v$ subunit; and
   iii) any combination of (i) and (ii),
and which have at least three fold increased adherence as compared to unmodified cells, the following:
   I) a first vector comprising a lentivirus nucleic acid sequence encoding at least one lentivirus structural protein, wherein said vector (1) comprises at least one defect in at least one gene encoding a lentivirus structural protein, and (2) comprises a defective packaging signal;
   II) a second vector comprising a lentivirus nucleic acid sequence comprising cis-acting sequence elements required for reverse transcription of the vector genome wherein said vector comprises a competent packaging signal; and
   III) a third vector comprising a nucleic acid sequence of a virus, wherein said third vector (1) expresses a viral envelope protein, and (2) comprises a defective packaging signal,
under conditions whereby recombinant lentivirus particles are produced.

2. The method of claim 1, wherein the second vector is deficient for expression of at least one lentivirus structural protein.

3. The method of claim 1, wherein the cells are HEK 293 cells.

4. The method of claim 1, wherein the first vector is a gag-pol expression vector, and wherein the vector comprises a defect in an env gene.

5. The method of claim 4, wherein the defect in the env gene is a deletion mutation.

6. The method of claim 1, wherein the first vector and the second vector each comprise a defect in an env gene.

7. The method of claim 1, wherein the third vector encodes a viral envelope protein that is not a lentivirus envelope protein.

8. The method of claim 7, wherein the third vector encodes a vesicular stomatitis virus G glycoprotein.

9. The method of claim 1, wherein the second vector comprises a heterologous nucleic acid.

10. The method of claim 1, wherein the lentivirus is a nonprimate lentivirus.

11. The method of claim 10, wherein the nonprimate lentivirus is equine infectious anemia virus (EIAV).

12. The method of claim 11, wherein the first vector is the plasmid pEV53B; the second vector is the plasmid pESIN6.1 CpuroW, and the third vector is the plasmid pCI-VSV-G.

13. The method of claim 1, wherein the vessel is selected from the group consisting of a flask, a bottle, a roller bottle, a dish, a slide, a tube, a cover slip, a plate and any combination thereof.

14. A method of producing recombinant EIAV particles in modified EIAV helper cells in a culture vessel, comprising: introducing into the modified EIAV helper cells, which are modified to comprise a stably integrated recombinant nucleic acid selected from the group consisting of:
   i) a nucleic acid encoding an integrin $\beta_3$ subunit;
   ii) a nucleic acid encoding an integrin $\alpha_v$ subunit; and
   iii) any combination of (i) and (ii),
and which have at least three fold increased adherence as compared to unmodified EIAV helper cells, the following:
   I) a first vector comprising an EIAV nucleic acid sequence encoding at least one EIAV structural protein, wherein said vector (1) comprises at least one defect in at least one gene encoding an EIAV structural protein, and (2) comprises a defective packaging signal;
   II) a second vector comprising an EIAV nucleic acid sequence comprising cis-acting sequence elements required for reverse transcription of the vector genome wherein said vector comprises a competent packaging signal; and
   III) a third vector comprising a nucleic acid sequence of a virus, wherein said third vector (1) expresses a viral envelope protein, and (2) comprises a defective packaging signal,
under conditions whereby recombinant EIAV particles are produced.

15. The method of claim 1, wherein the modified cells are lentivirus helper cells.

* * * * *

UNITED STATES PATENT AND TRADEMARK OFFICE
CERTIFICATE OF CORRECTION

PATENT NO. : 7,939,326 B2  
APPLICATION NO. : 11/118712  
DATED : May 10, 2011  
INVENTOR(S) : Olsen et al.

Page 1 of 1

It is certified that error appears in the above-identified patent and that said Letters Patent is hereby corrected as shown below:

Column 1, Line 14: Correct "by U.S. Government Grant No. HL 51818 awarded by"
to read -- by U. S. Government Grant Nos. HL 5181 and HL 68138 awarded by --
Line 58: Please correct "IIb" to read -- $\alpha_{IIb}$ --

Column 4, Line 52: Please correct "a 6-β4" to read -- $\alpha$ 6-$\beta$4 --

Column 8, Line 36: Please correct "5'TTTGGCGCGCCAGGTAAGATGGGAGAC-"
to read -- 5'TTTGGCGCGCCAGGTAAGATGGGAGAC- --

Column 17, Line 7: Please correct "$\alpha_v B_3$" to read -- $\alpha_v \beta_3$ --
Line 25: Please correct "$\alpha_v B_3$" to read -- $\alpha_v \beta_3$ --

Signed and Sealed this
Second Day of August, 2011

David J. Kappos
*Director of the United States Patent and Trademark Office*

UNITED STATES PATENT AND TRADEMARK OFFICE
CERTIFICATE OF CORRECTION

PATENT NO. : 7,939,326 B2  
APPLICATION NO. : 11/118712  
DATED : May 10, 2011  
INVENTOR(S) : Olsen et al.

Page 1 of 1

It is certified that error appears in the above-identified patent and that said Letters Patent is hereby corrected as shown below:

In the Specification:
Column 1, Lines 13-16, should read as follows:

"This invention was made with government support under Grant Nos. HL051818 and HL068138 awarded by the National Institutes of Health. The government has certain rights in the invention."

Signed and Sealed this
Twenty-fourth Day of December, 2013

Margaret A. Focarino
*Commissioner for Patents of the United States Patent and Trademark Office*

SEQUENCE LISTING

<160> NUMBER OF SEQ ID NOS: 2

<210> SEQ ID NO 1
<211> LENGTH: 35
<212> TYPE: DNA
<213> ORGANISM: Artificial
<220> FEATURE:
<223> OTHER INFORMATION: Synthetic oligonucleotide

<400> SEQUENCE: 1
tttggcgcgc caggtaagat gggagaccct ttgac        35

<210> SEQ ID NO 2
<211> LENGTH: 22
<212> TYPE: DNA
<213> ORGANISM: Artificial
<220> FEATURE:
<223> OTHER INFORMATION: Synthetic oligonucleotide

<400> SEQUENCE: 2
ctacttgatc cttctccttg ac        22